(12) United States Patent
Farritor et al.

(10) Patent No.: US 10,111,711 B2
(45) Date of Patent: *Oct. 30, 2018

(54) ROBOTIC SURGICAL DEVICES, SYSTEMS, AND RELATED METHODS

(71) Applicant: Board of Regents of the University of Nebraska, Lincoln, NE (US)

(72) Inventors: Shane Farritor, Lincoln, NE (US); Tyler Wortman, Grand Island, NE (US); Kyle Strabala, Pittsburgh, PA (US); Ryan McCormick, Arlington, VA (US); Amy Lehman, York, NE (US); Dmitry Oleynikov, Omaha, NE (US)

(73) Assignee: Board of Regents of the University of Nebraska, Lincoln, NE (US)

(*) Notice: Subject to any disclaimer, the term of this patent is extended or adjusted under 35 U.S.C. 154(b) by 0 days.

This patent is subject to a terminal disclaimer.

(21) Appl. No.: 14/800,423

(22) Filed: Jul. 15, 2015

(65) Prior Publication Data
US 2016/0015461 A1 Jan. 21, 2016

Related U.S. Application Data

(63) Continuation of application No. 13/546,831, filed on Jul. 11, 2012, now Pat. No. 9,089,353.
(Continued)

(51) Int. Cl.
*G05B 19/00* (2006.01)
*A61B 19/00* (2006.01)
(Continued)

(52) U.S. Cl.
CPC .......... *A61B 19/2203* (2013.01); *A61B 34/30* (2016.02); *A61B 90/30* (2016.02);
(Continued)

(58) Field of Classification Search
CPC ........ A61B 19/2203; A61B 2019/2223; A61B 2019/2242; A61B 2019/2234;
(Continued)

(56) References Cited

U.S. PATENT DOCUMENTS 3,870,264 A  3/1975 Robinson
3,989,952 A  11/1976 Hohmann
(Continued)

FOREIGN PATENT DOCUMENTS

CN  1082821918  12/2012
DE  102010040405  3/2012
(Continued)

OTHER PUBLICATIONS

Mack, Minimally Invasive and Robotic Surgery, 2001, Internet. p. 568-572.*
(Continued)

*Primary Examiner* — McDieunel Marc
(74) *Attorney, Agent, or Firm* — Davis, Brown, Koehn, Shors & Roberts, P.C.; Sean D. Solberg

(57) ABSTRACT

The embodiments relate to various medical device components, including components that are incorporated into robotic and/or in vivo medical devices. Certain embodiments include various modular medical devices for in vivo medical procedures.

21 Claims, 32 Drawing Sheets

Related U.S. Application Data

(60) Provisional application No. 61/506,384, filed on Jul. 11, 2011.

(51) Int. Cl.
*B25J 9/00* (2006.01)
*B25J 9/06* (2006.01)
*A61B 90/30* (2016.01)
*A61B 34/30* (2016.01)
*A61B 90/00* (2016.01)

(52) U.S. Cl.
CPC .............. *B25J 9/0087* (2013.01); *B25J 9/06* (2013.01); *A61B 90/361* (2016.02); *A61B 2034/302* (2016.02); *G05B 2219/40418* (2013.01); *Y10S 901/02* (2013.01); *Y10S 901/19* (2013.01)

(58) Field of Classification Search
CPC . A61B 2019/223; A61B 34/30; A61B 90/361; A61B 2034/302; B25J 9/0087; B25J 9/06; G05B 2219/40418; Y10S 901/02; Y10S 901/19
USPC ..... 700/245, 264; 600/102, 228, 229; 606/1, 606/130
See application file for complete search history.

(56) References Cited

U.S. PATENT DOCUMENTS

| | | |
|---|---|---|
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A * | 3/1999 | Mizuno ............... A61B 1/00048 600/102 |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |

(56) References Cited

U.S. PATENT DOCUMENTS

| | | | |
|---|---|---|---|
| 6,394,998 B1 | 5/2002 | Wallace et al. | |
| 6,398,726 B1 | 6/2002 | Ramans et al. | |
| 6,400,980 B1 | 6/2002 | Lemelson | |
| 6,408,224 B1 | 6/2002 | Okamoto et al. | |
| 6,424,885 B1 | 7/2002 | Niemeyer et al. | |
| 6,432,112 B2 | 8/2002 | Brock et al. | |
| 6,436,107 B1 | 8/2002 | Wang et al. | |
| 6,441,577 B2 | 8/2002 | Blumenkranz et al. | |
| 6,450,104 B1 | 9/2002 | Grant et al. | |
| 6,451,027 B1 | 9/2002 | Cooper et al. | |
| 6,454,758 B1 | 9/2002 | Thompson et al. | |
| 6,459,926 B1 | 10/2002 | Nowlin et al. | |
| 6,463,361 B1 | 10/2002 | Wang et al. | |
| 6,468,203 B2 | 10/2002 | Belson | |
| 6,468,265 B1* | 10/2002 | Evans | A61B 34/32 |
| | | | 600/103 |
| 6,470,236 B2 | 10/2002 | Ohtsuki | |
| 6,491,691 B1 | 12/2002 | Morley et al. | |
| 6,491,701 B2 | 12/2002 | Tierney et al. | |
| 6,493,608 B1 | 12/2002 | Niemeyer et al. | |
| 6,496,099 B2 | 12/2002 | Wang et al. | |
| 6,508,413 B2 | 1/2003 | Bauer et al. | |
| 6,512,345 B2 | 1/2003 | Borenstein | |
| 6,522,906 B1 | 2/2003 | Salisbury, Jr. et al. | |
| 6,544,276 B1 | 4/2003 | Azizi | |
| 6,548,982 B1 | 4/2003 | Papanikolopoulos et al. | |
| 6,554,790 B1 | 4/2003 | Moll | |
| 6,565,554 B1 | 5/2003 | Niemeyer | |
| 6,574,355 B2 | 6/2003 | Green | |
| 6,587,750 B2* | 7/2003 | Gerbi | G06F 19/3406 |
| | | | 128/897 |
| 6,591,239 B1 | 7/2003 | McCall et al. | |
| 6,594,552 B1 | 7/2003 | Nowlin et al. | |
| 6,610,007 B2 | 8/2003 | Belson et al. | |
| 6,620,173 B2 | 9/2003 | Gerbi et al. | |
| 6,642,836 B1 | 11/2003 | Wang et al. | |
| 6,645,196 B1 | 11/2003 | Nixon et al. | |
| 6,646,541 B1 | 11/2003 | Wang et al. | |
| 6,648,814 B2 | 11/2003 | Kim et al. | |
| 6,659,939 B2 | 12/2003 | Moll et al. | |
| 6,661,571 B1 | 12/2003 | Shioda et al. | |
| 6,671,581 B2 | 12/2003 | Niemeyer et al. | |
| 6,676,684 B1 | 1/2004 | Morley et al. | |
| 6,684,129 B2 | 1/2004 | Salisbury, Jr. et al. | |
| 6,685,648 B2 | 2/2004 | Flaherty et al. | |
| 6,685,698 B2 | 2/2004 | Morley et al. | |
| 6,687,571 B1 | 2/2004 | Byrne et al. | |
| 6,692,485 B1 | 2/2004 | Brock et al. | |
| 6,699,177 B1 | 3/2004 | Wang et al. | |
| 6,699,235 B2 | 3/2004 | Wallace et al. | |
| 6,702,734 B2 | 3/2004 | Kim et al. | |
| 6,702,805 B1 | 3/2004 | Stuart | |
| 6,714,839 B2 | 3/2004 | Salisbury, Jr. et al. | |
| 6,714,841 B1 | 3/2004 | Wright et al. | |
| 6,719,684 B2 | 4/2004 | Kim et al. | |
| 6,720,988 B1 | 4/2004 | Gere et al. | |
| 6,726,699 B1 | 4/2004 | Wright et al. | |
| 6,728,599 B2 | 4/2004 | Wright et al. | |
| 6,730,021 B2 | 5/2004 | Vassiliades, Jr. et al. | |
| 6,731,988 B1 | 5/2004 | Green | |
| 6,746,443 B1 | 6/2004 | Morley et al. | |
| 6,764,441 B2 | 7/2004 | Chiel et al. | |
| 6,764,445 B2 | 7/2004 | Ramans et al. | |
| 6,766,204 B2 | 7/2004 | Niemeyer et al. | |
| 6,770,081 B1 | 8/2004 | Cooper et al. | |
| 6,774,597 B1 | 8/2004 | Borenstein | |
| 6,776,165 B2 | 8/2004 | Jin | |
| 6,780,184 B2 | 8/2004 | Tanrisever | |
| 6,783,524 B2 | 8/2004 | Anderson et al. | |
| 6,785,593 B2 | 8/2004 | Wang et al. | |
| 6,788,018 B1 | 9/2004 | Blumenkranz | |
| 6,792,663 B2 | 9/2004 | Krzyzanowski | |
| 6,793,653 B2 | 9/2004 | Sanchez et al. | |
| 6,799,065 B1 | 9/2004 | Niemeyer | |
| 6,799,088 B2 | 9/2004 | Wang et al. | |
| 6,801,325 B2 | 10/2004 | Farr et al. | |
| 6,804,581 B2 | 10/2004 | Wang et al. | |
| 6,810,281 B2 | 10/2004 | Brock et al. | |
| 6,817,972 B2 | 11/2004 | Snow | |
| 6,817,974 B2 | 11/2004 | Cooper et al. | |
| 6,817,975 B1 | 11/2004 | Farr et al. | |
| 6,820,653 B1 | 11/2004 | Schempf et al. | |
| 6,824,508 B2 | 11/2004 | Kim et al. | |
| 6,824,510 B2 | 11/2004 | Kim et al. | |
| 6,832,988 B2 | 12/2004 | Sprout | |
| 6,832,996 B2 | 12/2004 | Woloszko et al. | |
| 6,836,703 B2 | 12/2004 | Wang et al. | |
| 6,837,846 B2 | 1/2005 | Jaffe et al. | |
| 6,837,883 B2* | 1/2005 | Moll | A61B 19/2203 |
| | | | 606/1 |
| 6,839,612 B2 | 1/2005 | Sanchez et al. | |
| 6,840,938 B1 | 1/2005 | Morley et al. | |
| 6,852,107 B2 | 2/2005 | Wang et al. | |
| 6,858,003 B2 | 2/2005 | Evans et al. | |
| 6,860,346 B2 | 3/2005 | Burt et al. | |
| 6,860,877 B1 | 3/2005 | Sanchez et al. | |
| 6,866,671 B2 | 3/2005 | Tierney et al. | |
| 6,870,343 B2 | 3/2005 | Borenstein et al. | |
| 6,871,117 B2 | 3/2005 | Wang et al. | |
| 6,871,563 B2 | 3/2005 | Choset et al. | |
| 6,879,880 B2 | 4/2005 | Nowlin et al. | |
| 6,892,112 B2 | 5/2005 | Wang et al. | |
| 6,899,705 B2 | 5/2005 | Niemeyer | |
| 6,902,560 B1 | 6/2005 | Morley et al. | |
| 6,905,460 B2 | 6/2005 | Wang et al. | |
| 6,905,491 B1 | 6/2005 | Wang et al. | |
| 6,911,916 B1 | 6/2005 | Wang et al. | |
| 6,917,176 B2 | 7/2005 | Schempf et al. | |
| 6,933,695 B2 | 8/2005 | Blumenkranz | |
| 6,936,001 B1 | 8/2005 | Snow | |
| 6,936,003 B2 | 8/2005 | Iddan | |
| 6,936,042 B2 | 8/2005 | Wallace et al. | |
| 6,943,663 B2 | 9/2005 | Wang et al. | |
| 6,949,096 B2 | 9/2005 | Davison et al. | |
| 6,951,535 B2 | 10/2005 | Ghodoussi et al. | |
| 6,965,812 B2 | 11/2005 | Wang et al. | |
| 6,974,411 B2 | 12/2005 | Belson | |
| 6,974,449 B2 | 12/2005 | Niemeyer | |
| 6,979,423 B2 | 12/2005 | Moll | |
| 6,984,203 B2 | 1/2006 | Tartaglia et al. | |
| 6,984,205 B2 | 1/2006 | Gazdzinski | |
| 6,991,627 B2 | 1/2006 | Madhani et al. | |
| 6,993,413 B2 | 1/2006 | Sunaoshi | |
| 6,994,703 B2 | 2/2006 | Wang et al. | |
| 6,994,708 B2 | 2/2006 | Manzo | |
| 6,997,908 B2 | 2/2006 | Carrillo, Jr. et al. | |
| 7,025,064 B2 | 4/2006 | Wang et al. | |
| 7,027,892 B2 | 4/2006 | Wang et al. | |
| 7,033,344 B2 | 4/2006 | Imran | |
| 7,039,453 B2 | 5/2006 | Mullick | |
| 7,042,184 B2 | 5/2006 | Oleynikov et al. | |
| 7,048,745 B2 | 5/2006 | Tierney et al. | |
| 7,053,752 B2 | 5/2006 | Wang et al. | |
| 7,063,682 B1 | 6/2006 | Whayne et al. | |
| 7,066,879 B2 | 6/2006 | Fowler et al. | |
| 7,066,926 B2 | 6/2006 | Wallace et al. | |
| 7,074,179 B2 | 7/2006 | Wang et al. | |
| 7,077,446 B2 | 7/2006 | Kameda et al. | |
| 7,083,571 B2 | 8/2006 | Wang et al. | |
| 7,083,615 B2 | 8/2006 | Peterson et al. | |
| 7,087,049 B2 | 8/2006 | Nowlin et al. | |
| 7,090,683 B2 | 8/2006 | Brock et al. | |
| 7,097,640 B2 | 8/2006 | Wang et al. | |
| 7,105,000 B2 | 9/2006 | McBrayer | |
| 7,107,090 B2 | 9/2006 | Salisbury, Jr. et al. | |
| 7,109,678 B2 | 9/2006 | Kraus et al. | |
| 7,118,582 B1 | 10/2006 | Wang et al. | |
| 7,121,781 B2 | 10/2006 | Sanchez et al. | |
| 7,125,403 B2 | 10/2006 | Julian et al. | |
| 7,126,303 B2 | 10/2006 | Farritor et al. | |
| 7,147,650 B2 | 12/2006 | Lee | |
| 7,155,315 B2 | 12/2006 | Niemeyer et al. | |
| 7,169,141 B2* | 1/2007 | Brock | A61B 90/36 |
| | | | 606/1 |

(56) References Cited

U.S. PATENT DOCUMENTS

| | | |
|---|---|---|
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 * | 7/2007 | Julian ............ A61B 17/00234 600/228 |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 3,021,358 A1 | 9/2011 | Doyle et al. |
| 8,179,073 B2 | 5/2012 | Farritor et al. |
| 8,353,897 B2 | 1/2013 | Doyle et al. |
| 9,089,353 B2 * | 7/2015 | Farritor ............ A61B 19/2203 |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszka et al. |
| 2002/0038077 A1 | 3/2002 | de la Torre et al. |
| 2002/0065507 A1 | 5/2002 | Zadno-Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth et al. |
| 2004/0138525 A1 | 7/2004 | Saadat |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 7/2008 | Rioux et al. |
| 2008/0164079 A1 | 7/2008 | Jacobsen |

(56) References Cited

U.S. PATENT DOCUMENTS

| | | |
|---|---|---|
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Scott |
| 2010/0204713 A1 | 8/2010 | Ruiz |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0098529 A1 | 4/2011 | Ostrovsky et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor |
| 2012/0253515 A1 | 10/2012 | Coste-Maniere et al. |
| 2013/0041360 A1 | 2/2013 | Farritor et al. |
| 2013/0131695 A1 | 5/2013 | Scarfogliero et al. |
| 2013/0345717 A1 | 12/2013 | Markvicka et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0303434 A1 | 10/2014 | Farritor et al. |
| 2015/0051446 A1 | 2/2015 | Farritor et al. |

FOREIGN PATENT DOCUMENTS

| | | |
|---|---|---|
| EP | 1354670 | 10/2003 |
| EP | 2286756 | 2/2011 |
| EP | 2286756 A1 | 2/2011 |
| EP | 2329787 | 8/2011 |
| EP | 2563261 | 3/2013 |
| JP | 2004144533 | 5/1990 |
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2001505810 | 5/2001 |
| JP | 2003220065 | 8/2003 |
| JP | 2004322310 | 6/2004 |
| JP | 2004180781 | 7/2004 |
| JP | 2004329292 | 11/2004 |
| JP | 2006508049 | 3/2006 |
| JP | 2009-106606 | 5/2009 |
| JP | 2010-533045 | 10/2010 |
| JP | 2010-536436 | 12/2010 |
| JP | 2011-504794 | 2/2011 |
| JP | 2011-045500 | 3/2011 |
| JP | 2011-115591 | 6/2011 |
| WO | WO 92/21291 | 12/1992 |
| WO | WO 0189405 | 11/2001 |
| WO | WO 02/082979 | 10/2002 |
| WO | WO 02/100256 | 12/2002 |
| WO | WO 2005/009211 | 2/2005 |
| WO | WO 2005044095 | 5/2005 |
| WO | WO 2006 005075 | 1/2006 |
| WO | WO 2006/079108 | 1/2006 |
| WO | WO 2006/052927 | 5/2006 |
| WO | WO2006079108 | 7/2006 |
| WO | WO 2007011654 | 1/2007 |
| WO | WO 2007/111571 | 10/2007 |
| WO | WO 2007/149559 | 12/2007 |
| WO | WO 2009023851 A1 | 2/2009 |
| WO | WO 2009/144729 | 12/2009 |
| WO | WO2010/042611 | 4/2010 |
| WO | WO2010/046823 | 4/2010 |
| WO | WO2010050771 A2 | 5/2010 |
| WO | WO 2011075693 | 6/2011 |
| WO | WO 2011/118646 A1 | 9/2011 |
| WO | WO 2011/135503 A1 | 11/2011 |
| WO | WO 2011135503 | 11/2011 |
| WO | WO 2013009887 | 1/2013 |
| WO | WO 2014011238 | 1/2014 |

OTHER PUBLICATIONS

Stoianovici et al., Robotic Tools for Minimally Invasive Urologic Surgery, 2002, Internet, p. 1-17.*
Cleary et al., State of the Art in Surgical Robotics: Clinical Applications and Technology Challenges, 2002, Internet, p. 1-26.*
Green et al., Telepresence Surgery, 1995, IEEE, p. 324-329.*
International Preliminary Report on Patentability from related case PCT/US2007/014567, dated Jan. 8, 2009, 11 pp.
International Search report and Written Opinion from international application No. PCT/US2012/41911, dated Mar. 13, 2013.
International Search Report and Written Opinion from international application No. PCT/US12/46274, dated Sep. 25, 2012.
International Search Report and Written Opinion from international application No. PCT/US2007/089191, dated Nov. 10, 2008, 20 pp.
"International Search Report and Written Opinion from international application No. PCT/US07/14567, dated Apr. 28, 2008, 19 pp."
International Search Report and Written Opinion of international application No. PCT/US2008/069822, dated Aug. 5, 2009, 12 pp.
International Search Report and Written Opinion of international application No. PCT/US2008/073334, dated Jan. 12, 2009, 11 pp.
International Search Report and Written Opinion of international application No. PCT/US2008/073369, dated Nov. 12, 2008, 12 pp.
International Search Report and Written Opinion issued in PCT/US11/46809, dated Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine mode," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.

(56) References Cited

OTHER PUBLICATIONS

Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
Macfarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Svstems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, I/4-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Stoianovici et al., "Robotic Tools for Minimally Invasive Urologic Surgery", Jan. 1, 2002, pp. 1-17.
Cleary et al., "State of the Art in Surgical Rootics: Clinical Applications and Technology Challenges", "Computer Aided Surgery", Jan. 1, 2002, pp. 312-328, vol. 6.
Green, "Telepresence Surgery", Jan. 1, 1995, Publisher: IEEE Engineering in Medicine and Biology.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 8005X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.

(56) References Cited

OTHER PUBLICATIONS

Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Franklin et al., "Prospective Comparison of Open vs. Laparoscopic Colon Surgery for Carcinoma: Five-Year Results," Dis Colon Rectum, 1996; 39: S35-S46.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.

Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MIMIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imagining," vol. 25, No. 1, Gastroenterology Nursing, pp. 24-27.
International Search Report and Written Opinion of international application No. PCT/US2010/061137, dated Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., "Wireless endoscopy," Gastrointestinal Endoscopy 2000; 51(6): 725-729.
Hanly et al., "Value of the SAGES Learning Center in introducing new technology," Surgical Endoscopy, 2004; 19(4):477-483.
Hanly et al., "Robotic Abdominal Surgery," The American Journal of Surgery 188 (Suppl.to Oct. 1994): 19S-26S, 2004.
Heikkinen et al., "Comparison of laparoscopic and open Nissen fundoplication two years after operation: A prospective randomized trial," Surgical Endoscopy, 2000; 14: 1019-1023.
Hissink, "Olympus Medical develops capsule camera technology," Dec. 2004, accessed Aug. 29, 2007, http://www.letsgodigital.org , 3 pp.
Horgan et al., "Technical Report: Robots in Laparoscopic Surgery," Journal of Laparoendoscopic & Advanced Surgical Techniques, 2001; 11(6): 415-419.
Palm, William, "Rapid Prototyping Primer" May 1998 (revised Jul. 30, 2002) (http://www.me.psu.edu/lamancusa/rapidpro/primer/chapter2.htm).
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.

(56) References Cited

OTHER PUBLICATIONS

Phee et al., "Development of Microrobotic Devices for Locomotion in the Human Gastrointestinal Tract," International Conference on Computational Intelligence, Robotics and Autonomous Systems (CIRAS 2001), Nov. 28-30, 2001, Singapore.

Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.

Preliminary Amendment filed Apr. 11, 2007, in related case U.S. Appl. No. 11/403,756, 7 pp.

Preliminary Amendment filed Jul. 30, 2008, in related case U.S. Appl. No. 12/171,413, 4 pp.

RCE and Amendment filed Jun. 13, 2007, in related case U.S. Appl. No. 11/403,756, 8 pp.

Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.

Rentschler et al., "Mobile In Vivo Biopsy Robot," IEEE International Conference on Robotics and Automation, Orlando, Florida, May 2006, pp. 4155-4160.

Rentschler et al., "Miniature in vivo Robots for Remote and Harsh Environments," IEEE Transactions on Information Technology in Biomedicine, Jan. 2006; 12(1): 66-75.

Rentschler et al., "An In Vivo Mobile Robot for Surgical Vision and Task Assistance," Journal of Medical Devices, Mar. 2007, vol. 1: 23-29.

Rentschler et al., "In vivo Mobile Surgical Robotic Task Assistance," 1 pg.

Rentschler et al., "In vivo Robotics during the NEEMO 9 Mission," Medicine Meets Virtual Reality, Feb. 2007, I pg.

Rentschler et al.., "In Vivo Robots for Laparoscopic Surgery," Studies in Health Technology and Infonnatics—Medicine Meets Virtual Reality, ISO Press, Newport Beach, CA, 2004a, 98: 316-322.

Rentschler et al., "Mechanical Design of Robotic In Vivo Wheeled Mobility," ASME Journal of Mechanical Design, 2006a, pp. I-II.

Rentschler et al., "Mobile In Vivo Camera Robots Provide Sole Visual Feedback for Abdominal Exploration and Cholecystectomy," Journal of Surgical Endoscopy, 20-I: 135-138, 2006b.

Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.

Rentschler et al., "Modeling, Analysis, and Experimental Study of In Vivo Wheeled Robotic Mobility," IEEE Transactions on Robotics, 22 (2): 308-321, 2005c.

Rentschler et al., "Natural Orifice Surgery with an Endoluminal Mobile Robot," The Society of American Gastrointestinal Endoscopic Surgeons, Dallas, TX, Apr. 2006d, 14 pp.

Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.

Rentschler et al., "Toward In Vivo Mobility," Studies in Health Technology and Informatics—Medicine Meets Virtual Reality, ISO Press, Long Beach, CA, 2005a, III: 397-403.

Response to Rule 312 Amendment in related case U.S. Appl. No. 11/695,944, dated Jan. 12, 2009, 2 pp.

Riviere et al., "Toward Active Tremor Canceling in Handheld Microsurgical Instruments," IEEE Transactions on Robotics and Automation, Oct. 2003, 19(5): 793-800.

Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.

Rosen et al., "Objective Laparoscopic Skills Assessments of Surgical Residents Using Hidden Markov Models Based on Haptic Information and Tool/Tissue Interactions," Studies in Health Technology and Infonnatics-Medicine Meets Virtual Reality, Jan. 2001, 7 pp.

Rosen et al., "Spherical Mechanism Analysis of a Surgical Robot for Minimally Invasive Surgery—Analytical and Experimental Approaches," Studies in Health Technology and Infonnatics—Medicine Meets Virtual Reality, pp. 442-448, Jan. 2005.

Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.

Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.

Ruurda et al., "Robot-Assisted surgical systems: a new era in laparoscopic surgery," Ann R. Coll Surg Engl., 2002; 84: 223-226.

Ruurda et al., "Feasibility of Robot-Assisted Laparoscopic Surgery," Surgical Laparoscopy, Endoscopy & Percutaneous Techniques, 2002; 12(1):41-45.

Sackier et al., "Robotically assisted laparoscopic surgery," Surgical Endoscopy, 1994; 8: 63-66.

Salky, "What is the Penetration of Endoscopic Techniques into Surgical Practice?" Digestive Surgery, 2000; 17:422-426.

Satava, "Surgical Robotics: The Early Chronicles," Surgical Laparoscopy, Endoscopy & Percutaneous Techniques, 2002; 12(1): 6-16.

Schippers et al., (1996) "Requirements and Possibilities of Computer-Assisted Endoscopic Surgery," In: Computer Integrated Surgery: Technology and Clinical Applications, pp. 561-565.

Schurr et al., "Robotics and Telemanipulation Technologies for Endoscopic Surgery," Surgical Endoscopy, 2000; 14: 375-381.

Schwartz, "In the Lab: Robots that Slink and Squirm," The New York Times, Mar. 27, 2007, 4 pp.

Sharp LL-151-3D, http://www.sharp3d.com, 2006, 2 pp.

Slatkin et al., "The Development of a Robotic Endoscope," Proceedings of the 1995 IEEE International Conference on Robotics and Automation, pp. 162-171, 1995.

Smart Pill "Fantastic Voyage: Smart Pill to Expand Testing," http://www.smartpilldiagnostics.com, Apr. 13, 2005, 1 pg.

Southern Surgeons Club (1991), "A prospective analysis of 1518 laparoscopic cholecystectomies," N. Eng. 1 Med. 324 (16): 1073-1078.

Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.

Stiff et al.., "Long-term Pain: Less Common After Laparoscopic than Open Cholecystectomy," British Journal of Surgery, 1994; 81: 1368-1370.

Strong, et al., "Efficacy of Novel Robotic Camera vs. a Standard Laproscopic Camera," Surgical Innovation vol. 12, No. 4, Dec. 2005, Westminster Publications, Inc., pp. 315-318.

Suzumori et al., "Development of Flexible Microactuator and its Applications to Robotics Mechanisms," Proceedings of the IEEE International Conference on Robotics and Automation, 1991: 1622-1627.

Taylor et al., "A Telerobotic Assistant for Laparoscopic Surgery," IEEE Eng Med Biol, 1995; 279-287.

Tendick et al.. (1993), "Sensing and Manipulation Problems in Endoscopic Surgery: Experiment, Analysis, and Observation," Presence 2( 1): 66-81.

Flynn et al, "Tomorrow's surgery: micromotors and microrobots for minimally invasive procedures," Minimally Invasive Surgery & Allied Technologies, 1998; 7(4): 343-352.

Guber et al., "Miniaturized Instrument Systems for Minimally Invasive Diagnosis and Therapy," Biomedizinische Technic. 2002, Band 47, Erganmngsband 1: 198-201.

Franzino, "The Laprotek Surgical System and the Next Generation of Robotics," Surg Clin North Am, 2003 83(6): 1317-1320.

\* cited by examiner

4-Bar Linkage

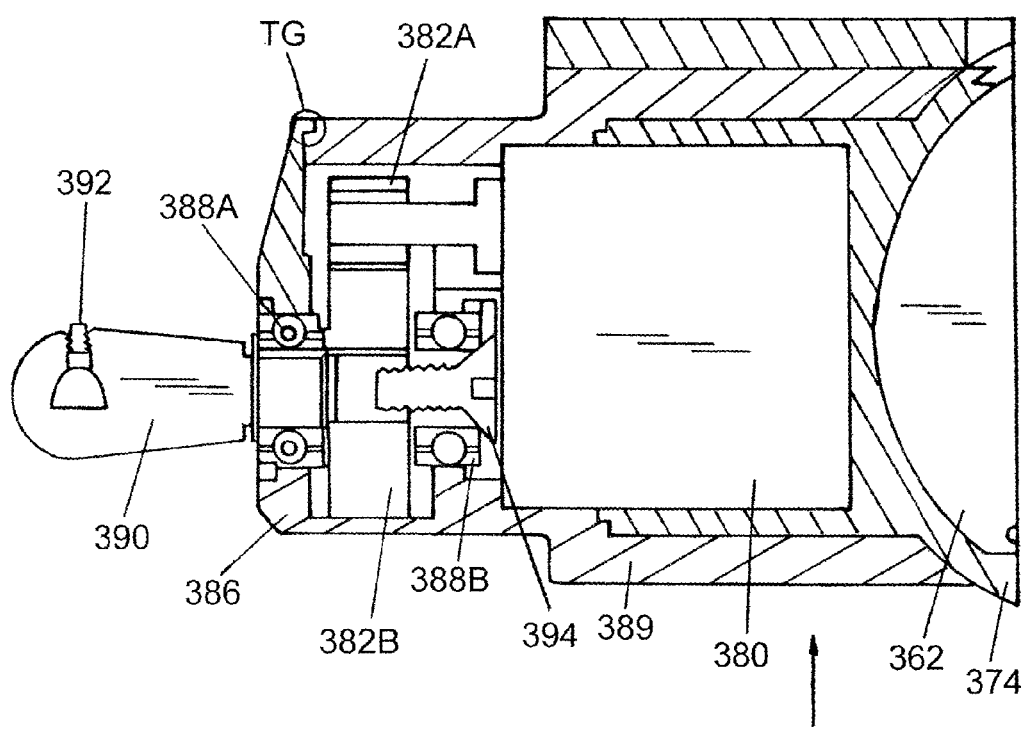

ROBOTIC SURGICAL DEVICES, SYSTEMS, AND RELATED METHODS

CROSS REFERENCE TO RELATED APPLICATIONS

This application claims priority from U.S. application Ser. No. 13/546,831, filed Jul. 11, 2012 and entitled "Robotic Surgical Devices, Systems and Related Methods," which claims priority from U.S. Provisional Application 61/506,384, filed Jul. 11, 2011, and entitled "Robotic Surgical Devices, Systems and Related Methods," which is hereby incorporated herein by reference in its entirety.

GOVERNMENT SUPPORT

This invention was made with government support under Grant No. W81XWH-08-2-0043 awarded by the U.S. Army Medical Research and Materiel Command within the Department of Defense; Grant No. NNX10AJ26G awarded by the National Aeronautics and Space Administration; and Grant No. DGE-1041000 awarded by the National Science Foundation. Accordingly, the government has certain rights in this invention.

TECHNICAL FIELD

The embodiments disclosed herein relate to various medical devices and related components, including robotic and/or in vivo medical devices and related components. Certain embodiments include various robotic medical devices, including robotic devices that are disposed within a body cavity and positioned using a support component disposed through an orifice or opening in the body cavity. Further embodiments relate to methods of operating the above devices.

BACKGROUND

Invasive surgical procedures are essential for addressing various medical conditions. When possible, minimally invasive procedures such as laparoscopy are preferred. However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

DETAILED DESCRIPTION

Figure 1:
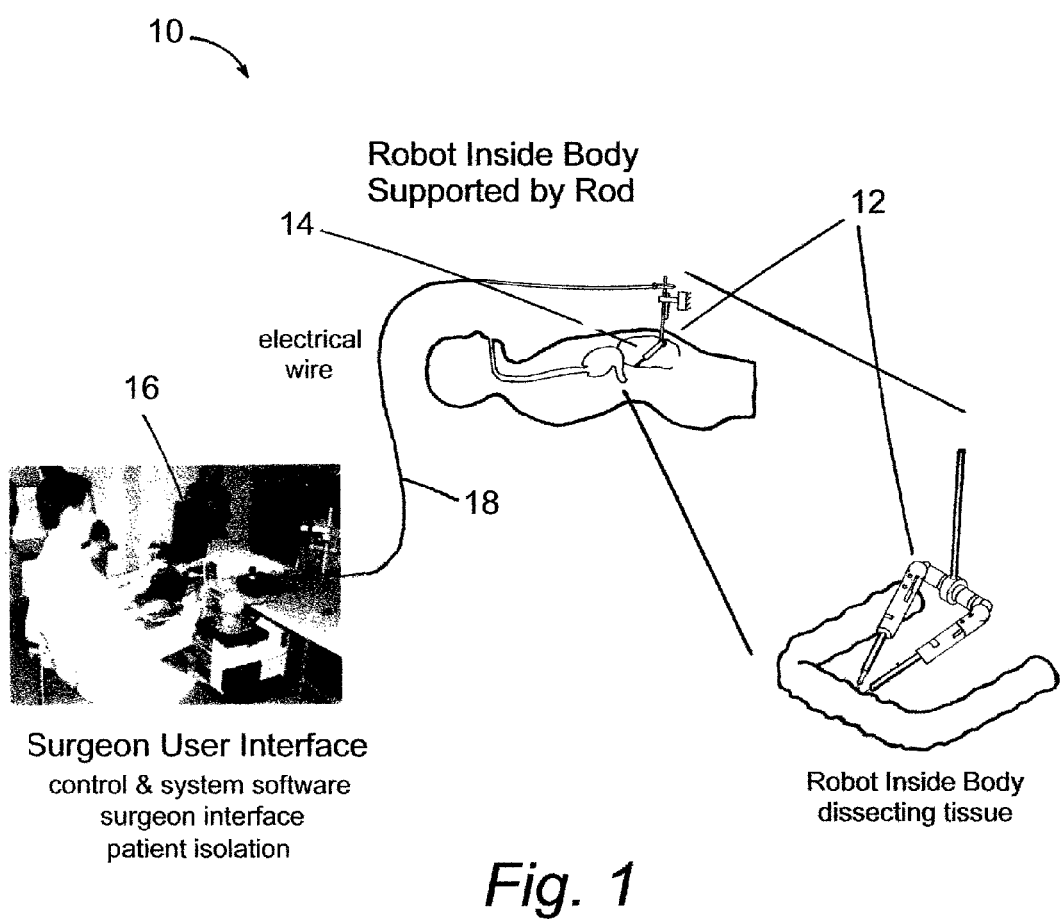
FIG. 1 is a diagram showing a system including a robotic device in use inside a body.

The various systems and devices disclosed herein relate to devices for use in medical procedures and systems. More specifically, various embodiments relate to various medical devices, including robotic devices and related methods and systems.

It is understood that the various embodiments of robotic devices and related methods and systems disclosed herein can be incorporated into or used with any other known medical devices, systems, and methods.

For example, the various embodiments disclosed herein may be incorporated into or used with any of the medical devices and systems disclosed in copending U.S. application Ser. No. 12/192,779 (filed on Aug. 15, 2008 and entitled "Modular and Cooperative Medical Devices and Related Systems and Methods"), Ser. No. 11/932,441 (filed on Oct. 31, 2007 and entitled "Robot for Surgical Applications"), Ser. No. 11/695,944 (filed on Apr. 3, 2007 and entitled "Robot for Surgical Applications"), Ser. No. 11/947,097 (filed on Nov. 27, 2007 and entitled "Robotic Devices with Agent Delivery Components and Related Methods), Ser. No. 11/932,516 (filed on Oct. 31, 2007 and entitled "Robot for Surgical Applications"), Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), Ser. No. 12/171,413 (filed on Jul. 11, 2008 and entitled "Methods and Systems of Actuation in Robotic Devices"), 60/956,032 (filed on Aug. 15, 2007), 60/983,445 (filed on Oct. 29, 2007), 60/990,062 (filed on Nov. 26, 2007), 60/990,076 (filed on Nov. 26, 2007), 60/990,086 (filed on Nov. 26, 2007), 60/990,106 (filed on Nov. 26, 2007), 60/990,470 (filed on Nov. 27, 2007), 61/025,346 (filed on Feb. 1, 2008), 61/030,588 (filed on Feb. 22, 2008), 61/030,617 (filed on Feb. 22, 2008), U.S. Pat. No. 8,179,073 (issued May 15, 2011, and entitled "Robotic Devices with Agent Delivery Components and Related Methods"), Ser. No. 12/324,364 (filed Nov. 26, 2008, U.S. Published App. 2009/0171373 and entitled "Multifunctional Operational Component for Robotic Devices"), Ser. No. 13/493,725 (filed Jun. 11, 2012 and entitled "Methods, Systems, and Devices Relating to Surgical End Effectors"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

FIG. 1 depicts an exemplary system 10 that includes a robotic surgical device 12 disposed within the inflated peritoneal cavity 14 of a patient. It is understood that the various device and system embodiments disclosed herein, including the system 10 of FIG. 1, can be used for a variety of surgical procedures and tasks including, but not limited to, tissue biopsy, tissue dissection, or tissue retraction. For example, as shown in FIG. 1 in accordance with one embodiment, the device 12 can be used to dissect tissue in the peritoneal cavity 14. In this system 10 embodiment, a user (such as, for example, a surgeon) operates a user interface 16 to control the device 12. The interface 16 is operably coupled to the device 12 by a cable 18 or other type of physical connection that provides for electronic and/or electrical communication back and forth between the interface 16 and the device 12. Alternatively, the interface 16 can be operably coupled to the device 12 wirelessly. It is understood that the device embodiments disclosed herein can also be used with any other known system, including any of the systems disclosed in the various patent applications incorporated by reference above and elsewhere herein.

Figure 2A:
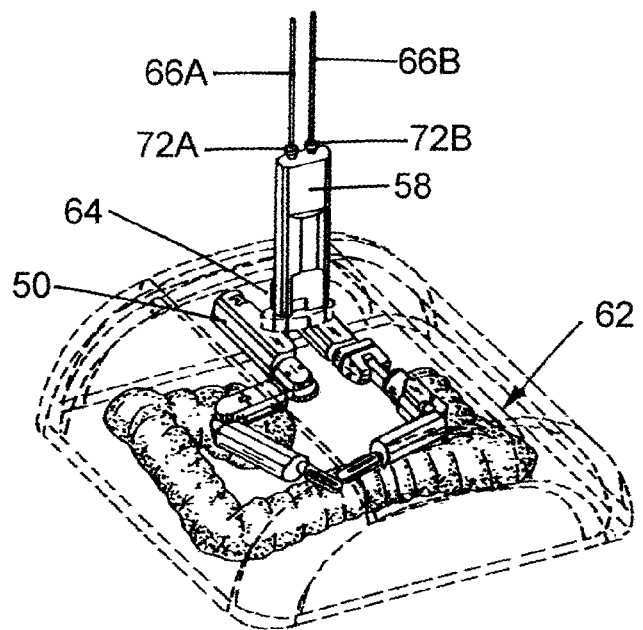
FIG. 2A is a perspective view of a modular medical device within a body cavity, according to another embodiment.
Figure 2B:
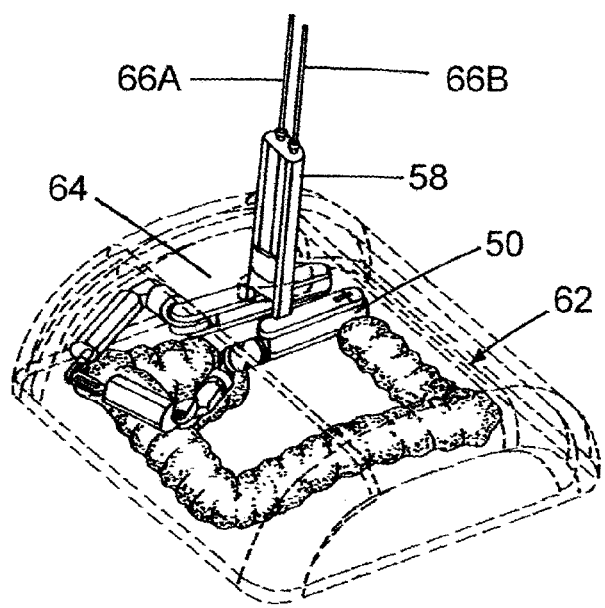
FIG. 2B is a perspective view of the modular device of FIG. 2A in a different position.
Figure 2C:
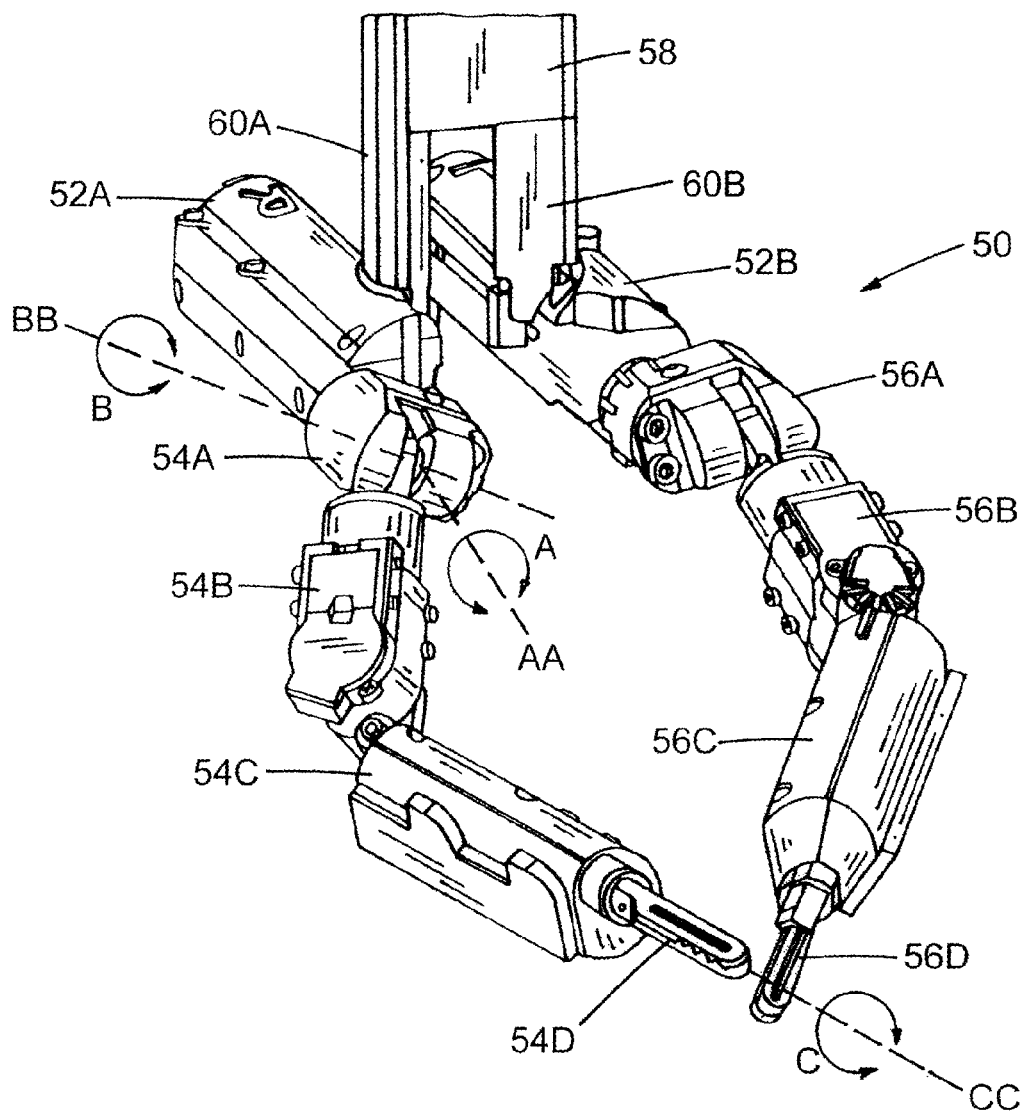
FIG. 2C is a perspective close-up view of a portion of the device of FIG. 2A.

FIGS. 2A-2C depict a robotic medical device 50 positioned within a patient's body cavity 62, in accordance with one implementation. According to one embodiment, the device 50 is an in vivo device 50. This device embodiment 50 as shown includes a body 52 that has two components 52A, 52B, which in this embodiment are cylindrical components 52A, 52B. In the embodiment depicted in FIG. 2C, the two components 52A, 52B are not coupled directly to each other. Alternatively, the two components 52A, 52B can be coupled to each other. In a further alternative, the body 52 (and any body of any device embodiment disclosed herein) can be a single component and further can be any of the device body embodiments disclosed in the various patent applications incorporated by reference above and elsewhere herein.

The body 52 is coupled to two arms 54, 56. In the implementation shown, the body component 52A is coupled to arm 54 and body component 52B is coupled to arm 56. In addition, the body 52 is also coupled to a support component 58. In this embodiment, the support component 58 is configured to be positioned over two support rods 66A, 66B as best shown in FIGS. 2A and 2B. The component 58 also has a first support leg 60A that is coupled to the first body component 52A and a second support leg 60B that is coupled to the second body component 52B. Alternatively, the support component 58 can be a single, integral component coupled to the body 52.

Each of the arms 54, 56 have a first joint 54A, 56A (each of which can also be referred to as a "shoulder joint") that is coupled to the body components 52A, 52B. Each first joint 54A, 56A is coupled to a first link 54B, 56B that is rotatably coupled to a second link 54C, 56C. In addition, each arm 54, 56 also has an operational component 54D, 56D coupled to the second link 54C, 56C. It is understood that the operational components 54D, 56D (and any of the operational components on any of the embodiments disclosed herein) can be any known operational components, including any of the operational components disclosed in the various patent applications incorporated by reference above and elsewhere herein.

As mentioned above, the first links 54B, 56B are coupled to the body 52 via shoulder joints 54A, 56A. As shown, each shoulder joint 54A, 56A is a joint having two axes of rotation. For example, joint 54A can rotate as shown by arrow A around axis AA that corresponds to the longitudinal axis of the body 52 while also being coupled to the first link 54B such that the link 54B can further rotate as shown by arrow B around axis BB that is perpendicular to axis AA that corresponds to the longitudinal axis of the body 52. Joint 56A has similar axes of rotation. Alternatively, any known joint can be used to couple the first links 54B, 56B to the body 52.

The operational components 54D, 56D, according to one implementation, are coupled to the second links 54C, 56C, respectively, such that each of the operational components 54D, 56D can rotate. For example, operational component 54D can rotate as shown by arrow C around axis CC corresponding to the longitudinal axis of the link 54C to which the component 54D is attached. Operational component 56D can rotate in a similar fashion. In addition, each of the operational components 54D, 56D can also be actuated to move between at least two configurations, such as an open configuration and a closed configuration. Alternatively, the operational components 54D, 56D can be coupled to the links 54C, 56C such that the operation components can be moved or actuated in any known fashion.

According to one embodiment, the operational components 54D, 56D are also removable from the second links 54C, 56C, such that the components 54D, 56D are interchangeable with other components configured to perform other/different types of procedures. In the embodiment depicted in FIG. 2C, both operational components 54D, 56D are graspers. Alternatively, either or both of the components can be cautery devices, suturing devices, grasping devices, imaging devices, operational arm devices, sensor devices, lighting devices or any other known types of devices or components for use in surgical procedures.

It is understood that the device 50 in this embodiment contains the motors (also referred to as "actuators," and intended to include any known source of motive force) that provide the motive force required to move the arms 54, 56 and the operational components 54D, 56D. In other words, the motors are contained within the device 50 itself (either in the body 52, the arms 54, 56 or both), rather than being located outside the patient's body.

In use, as best shown in FIGS. 2A and 2B, the device 50 is positioned inside a patient's body cavity. For example, in the schematic depict of FIGS. 2A and 2B, the body cavity is the peritoneal cavity 62. According to one implementation, the device 50 can be inserted through a single orifice by physically separating the device 50 into separate, smaller components and inserting those components through the single orifice. In one example, the device 50 can be separated into two "halves," in which one component consists of the first body component 52A coupled to the first arm 54 and the other component consists of the second body component 52B coupled to the second arm 56. Alternatively, this device 50 or any device contemplated herein can be separated into any two or more separable components. In the embodiment depicted in FIG. 2C, the device 50 is first separated into the two components as described above and then each of the two components are inserted in consecutive fashion through the orifice into the body cavity. In accordance with one implementation, due to the limitations associated with the amount of space in the cavity, each of the components can form a sequence of various configurations that make it possible to insert each such component into the cavity. That is, each component can be "stepped through" a sequence of configurations that allow the component to be inserted through the orifice and into the cavity.

According to one embodiment as best shown in FIGS. 2A and 2B, the support component 58 (including the support rods 66A, 66B) is configured to maintain the device 50 in the desired positioned within the cavity 62. The component 58, which is coupled to the body 52, is disposed through an orifice or any other kind of opening in the body cavity wall 64 such that the distal portion of the component 58 coupled to the body 52 is disposed within the body cavity 62 while the proximal portion is disposed outside of the patient's body and is attached to an external component 61 so as to provide stability or fixed positioning for the device 50.

More specifically, the two support rods 66A, 66B are coupled to the device 50. That is, the first support rod 66A is coupled to the first body component 52A and the second support rod 66B is coupled to the second body component 52B. Alternatively, the body 52 can be a single component and is coupled to both support rods 66A, 66B. As discussed above, this embodiment also has a support component 58 that is disposed over the support rods 66A, 66B (or alternatively, the support rods 66A, 66B are disposed within the support component 58) and positioned against or coupled to the body 52. As best shown in FIG. 2E, the component 58 defines two lumens 68A, 68B that are disposed through the length of the tube component 58. In some embodiments, an access lumen (not shown) is disposed through a substantially central or middle portion of the component 58, with the two rod lumens 68A, 68B disposed on either side of the access lumen. The rod lumens 68A, 68B are configured to receive the support rods 66A, 66B such that the component 58 can be positioned over the support rods 66A, 66B and against the body 52 of the device. The access lumen is configured to receive and provide access for any tools or endoscopes such that the tools or endoscopes can be inserted through the access lumen and into the body cavity to provide additional functionality in combination with the device 50.

In this embodiment, the support rods 66A, 66B are held in place within the component 58 (or the component 58 is held in place over the support rods 66A, 66B) using two attachment components 72A, 72B, each of which is configured to attach to one of the support rods 66A, 66B, as shown in FIG. 2A. In the specific embodiment shown in FIG. 2A, the attachment components 72A, 72B are threaded nuts, and after the support component 58 is disposed over the two support rods 66A, 66B, the threaded nut 72A is threadably coupled to the support rod 66A and the wing nut 72B is threadably coupled to the support rod 66B to hold the component 58 in place. Alternatively, the attachment components 72A, 72B can be any known attachment components for holding the component 58 in place.

Figure 2D:
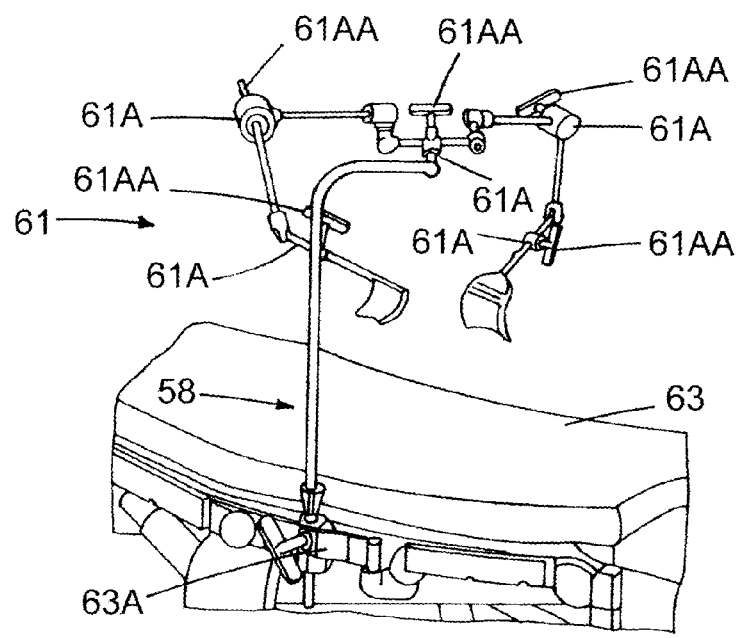
FIG. 2D is an image of an iron intern used to support the device of FIG. 1A.
Figure 2E:
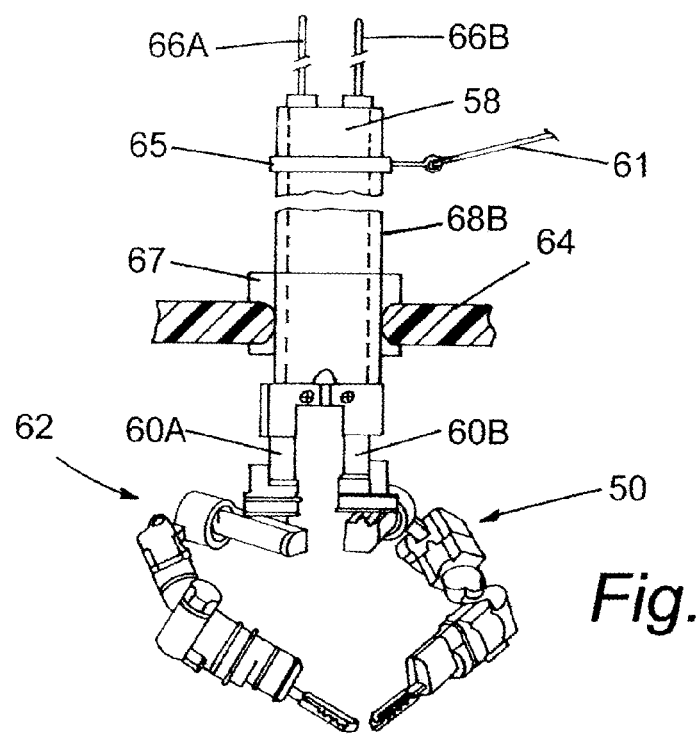
FIG. 2E is a perspective close-up view of a portion of the iron intern of FIG. 2D supporting the device of FIG. 2A.

FIGS. 2D-2E depict an external component 61 and port 67 that support device 50 while positioned within a patient's body cavity 62, in accordance with one implementation. According to this implementation, the device 50 is maintained in a desired position or location within the body cavity of the patient using an external component 61 that has a clamp 65 that is removably attached to support component 58. In use, the support legs 60A, 60B and the support component 58 are disposed through an opening in the body cavity wall such that the distal end of the legs 60A, 60B and the distal end of the support component 58 are positioned within the body cavity while the proximal end of the legs 60A, 60B and support component 58 are disposed outside of the patient's body. The external component 61 is coupleable to a proximal portion of the support component 58. In this embodiment, the clamp 65 couples to support component 58 to hold the support component 58 and thus the legs 60A, 60B and device 50 in the desired position. Alternatively, the external component 61 can have any known attachment component that is capable of removably coupling to or attaching to support component 58 and support legs 60A, 60B.

As best shown in FIG. 2D, an external component 61 can be an iron intern (Automated Medical Products Corp.) that includes several sections connected by joints 61A that can be loosened and locked using knobs 61AA to allow the iron intern to be positioned in various orientations. The external component 61 can be attached to rails 63A on any standard surgical table 63 or any other appropriate surface to provide support for device.

In use, according to one embodiment as best shown in FIG. 2E, the device 50 is positioned within the body cavity of the patient and the support legs 60A, 60B and support component 58 are positioned through a port 67 positioned in the hole or opening in the body cavity wall 64. In this embodiment, the port 67 is a gel port 67 through which the legs 60A, 60B and support component 58 can be disposed while still maintaining a fluidic seal that allows for the body cavity of the patient to be inflated. Alternatively, any known port that provides access for the legs 60A, 60B and support component 58 while maintaining a fluidic seal can be used.

FIGS. 3A-3L depict another embodiment of a robotic medical device 100. This device embodiment 100 as shown includes a body 102 having two cylindrical components 102A, 102B. The device has two arms 106, 108 that are coupled to the body 102. More specifically, the first arm 106 is rotatably coupled to the first cylindrical component 102A and the second arm 108 is rotatably coupled to the second cylindrical component 102B. The first arm 106 has a first link 106A that is coupled to the first component 102A, a second link 106B that is coupled to the first link 106A, and a third link 106C coupled to the second link 106B. Similarly, the second arm 108 has a first link 108A that is coupled to the second component 102B, a second link 108B that is coupled to the first link 108A, and a third link 108C coupled to the second link 108B. The first arm 106 has an operational component 106D coupled to the third link 106C, and the second arm 108 has an operational component 108D coupled to the third link 108C. In addition, the body 102 is also coupled to a support component 105, which is in turn, connected to support rods 103A and 103B.

The first link 106A is coupled to the first component 102A such that the first link can rotate around an axis parallel to the longitudinal axis of the first component 102A. As best shown in FIG. 3B, first component 102A includes a motor housing 102C that houses motor 101 and actuation mechanism 101A for first joint 101B. In this embodiment, the actuation mechanism 101A includes spur gear 101D that is rigidly attached to output shaft 101C of motor 101. As the motor output shaft 101C turns, spur gear 101D rotates spur gear 107, which is radially constrained with rotational shaft 107A through a flat 107B attached to both 107A and the bore of 107. 107A is supported with two flanged ball bearings 107C and 107D. Flanged ball bearing 107D is seated in the lower cap 102D of housing 102C. Rotational shaft 107A is attached to first link 106A via attachment 110 using, for example, a bolt. First link 108A is similarly coupled to the second component 102B such that the first link can rotate around an axis parallel to the longitudinal axis of the second component 102B.

The second link 106B is coupled to the first link 106A such that the second link 106B can rotate around an axis parallel to the longitudinal axis of first link 106A. As best shown in FIG. 3C, first link 106A includes motor housing half 109 comprising attachment 110. A second motor housing half (not shown) is configured similarly to motor housing half 109 and attaches to motor housing half 109 via attachment 110 using, for example, bolts to form a complete motor housing for first link 106A. The joint between first link 106A and second link 106B is actuated from a motor 112 located inside the motor housing. Encoder 113 provides position information to the interface (not shown) for motor 112. A planetary gearhead 111 is attached to motor 112 by way of mating threading on the motor 112 and planetary gearhead 111. Gearhead 111 is rigidly attached to gear housing 122 by use of epoxy to prevent rotation and translation of the motor assembly. Spur gear 123 is rigidly attached to the output shaft 111A of gearhead 111. As spur gear 123 is rotated by the motor 112, torque is transmitted to spur gear 115, which is rigidly attached to shaft 116. Shaft 116 is supported by ball bearings 117 and 118, housed in gear housing 122, and attaches to second link 106B. A button socket cap bolt 119 is threaded into shaft 116, preventing lateral translation of shaft 116. The second link 108B is similarly configured and coupled to first link 108A.

The second link 106B is configured such that, in addition to rotating around an axis parallel to the longitudinal axis of first link 106A, it can rotate around an axis perpendicular to the longitudinal axis of first link 106A. As best shown in FIGS. 3D and 3E, second link 106B comprises mirrored motors 130A and 130B and associated gears and shafts. Motor 130A and its associated gears and shafts are configured to rotate second link 106B in an axis perpendicular to the longitudinal axis of first link 106A. Shaft 116 from first link 106A includes a bore through which rotational shaft 133A of second link 106B inserts and attaches. Rotational shaft 133A and the bore of shaft 116 are constrained such that the rotation of rotational shaft 133A is fixed relative to shaft 116. Ball bearings 136A and 137A, which are housed in the motor housing 134, support rotational shaft 133A. A spur gear 131A is rigidly attached to shaft 133A and bolt 138A constrains rotational shaft 133A axially. Rotational shaft 133A is rotated as motor 130A is actuated, rotating spur gear 132A, which is rigidly attached to output shaft 135A of motor 130A. Motor 130A is constrained relative to housing 134 using, for example, bolts which go through housing 134. Gear cover 139A covers the moving gears to prevent outside objects from contacting the moving gears 131A, 132A.

The third link 106C is coupled to the second link 106B such that the third link can rotate around an axis perpendicular to the longitudinal axis of second link 106B. Motor 130B and its associated gears and shafts are configured to rotate shaft 140, which attaches to third link 106C, in an axis perpendicular to the longitudinal axis of second link 106B. As best shown in FIG. 3E, motor 130B is configured to actuate its associated gears and shafts in a manner similar to motor 130A and its associated gears and shafts.

Figure 3A:
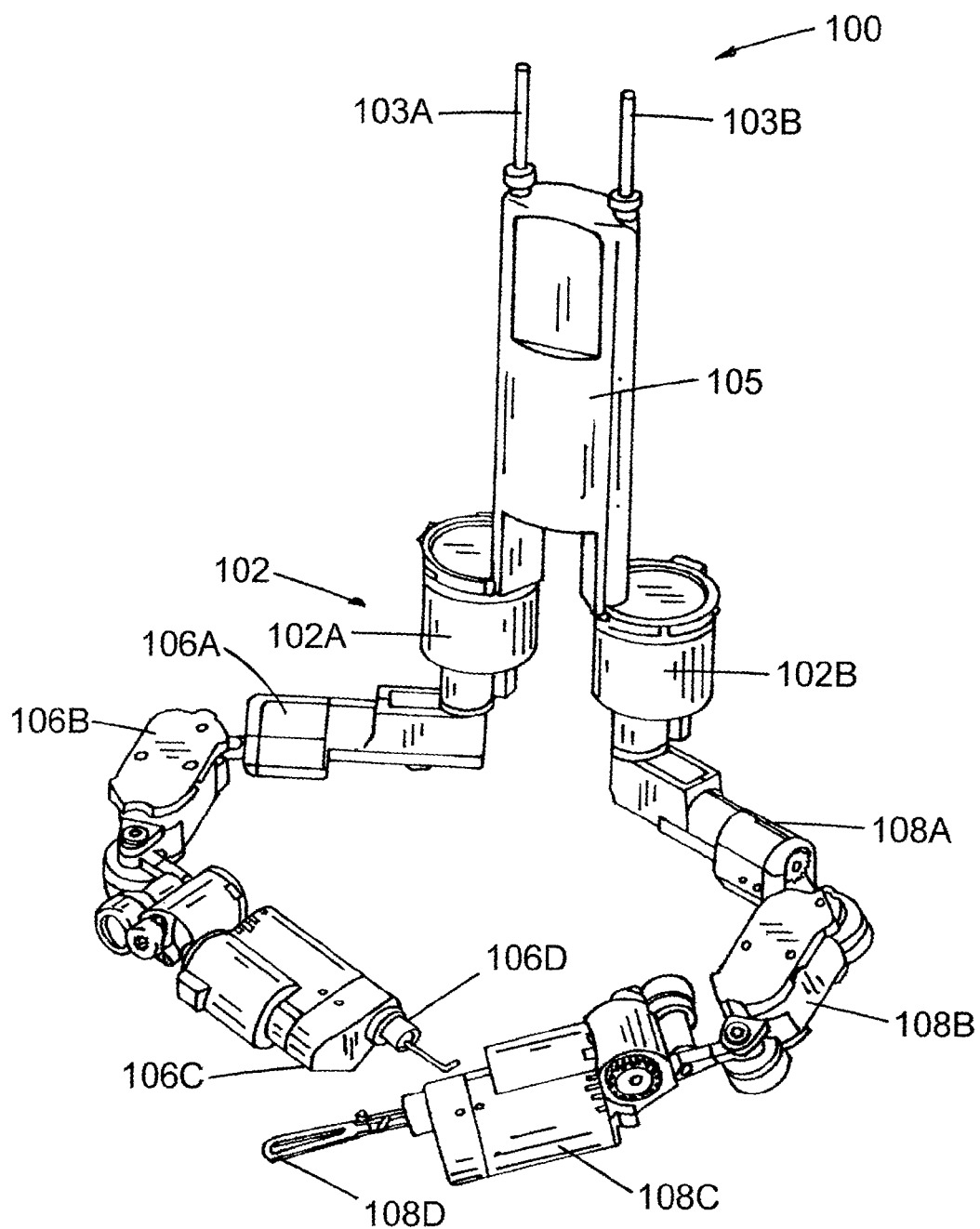
FIG. 3A is a perspective view of a modular medical device, according to another embodiment.
Figure 3B:
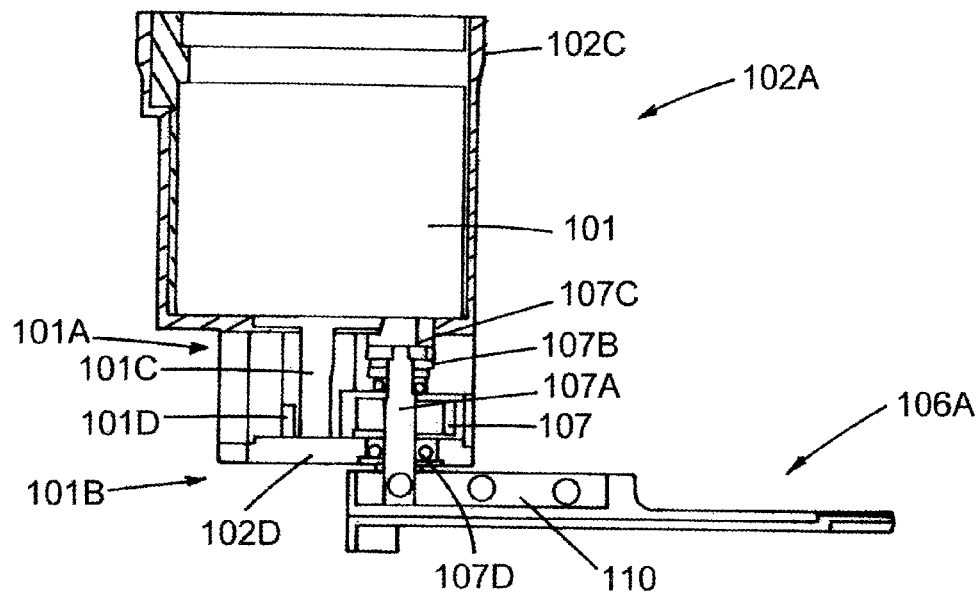
FIG. 3B is a cutaway close-up view of a portion of the device of FIG. 3A.
Figure 3C:
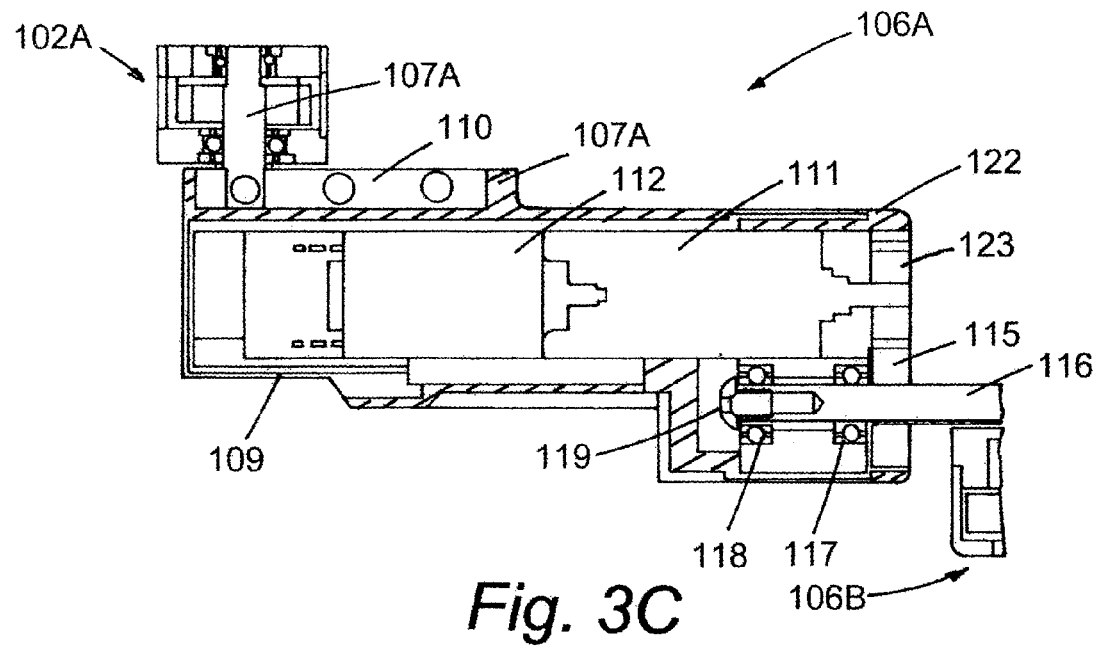
FIG. 3C is a cutaway close-up view of a portion of the device of FIG. 3A.
Figure 3D:
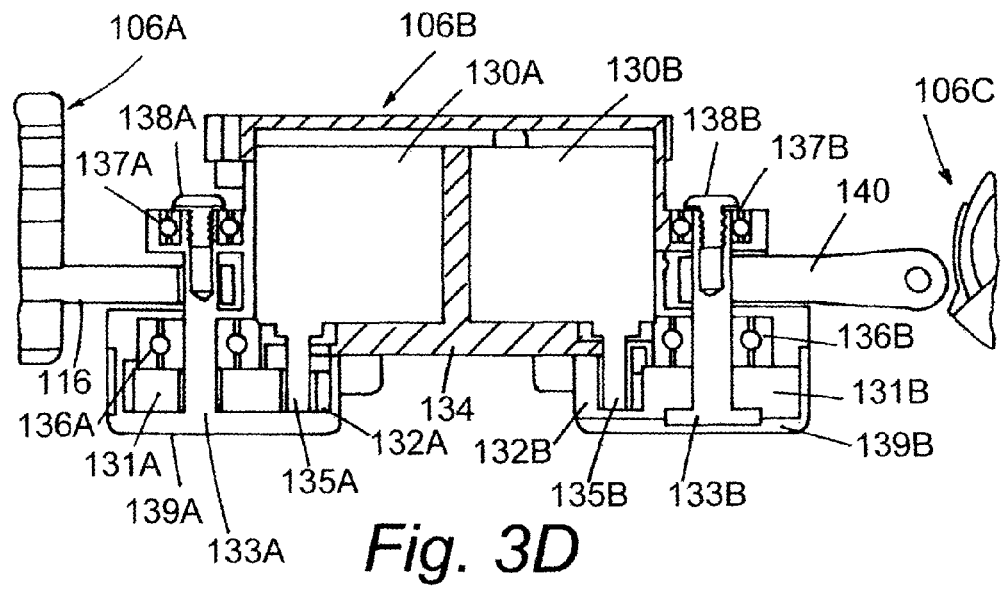
FIG. 3D is a cutaway close-up view of a portion of the device of FIG. 3A.
Figure 3E:
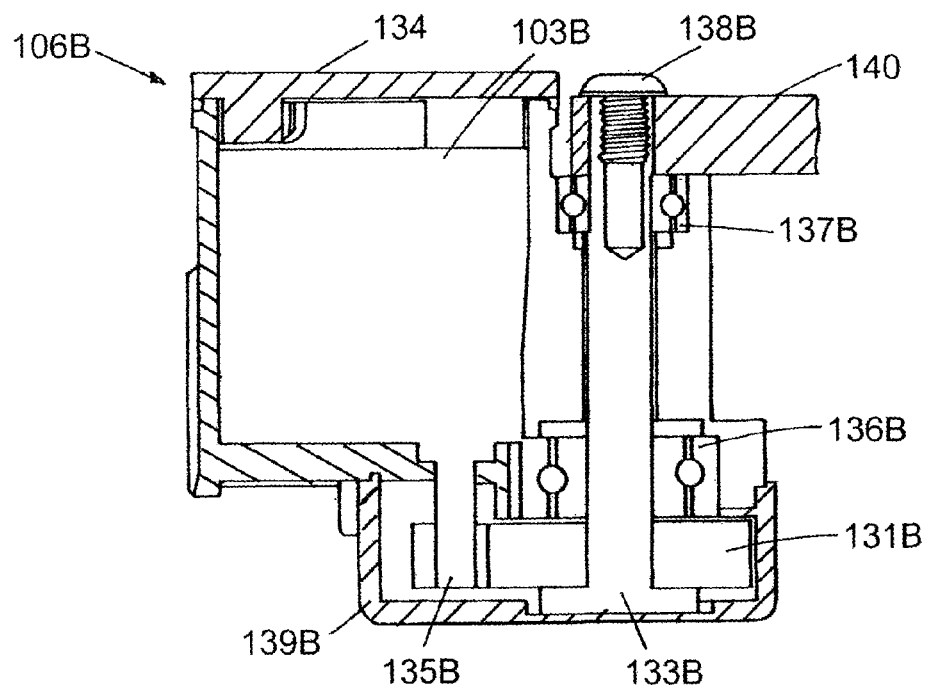
FIG. 3E is a cutaway close-up view of a portion of the device of FIG. 3A.
Figure 3F:
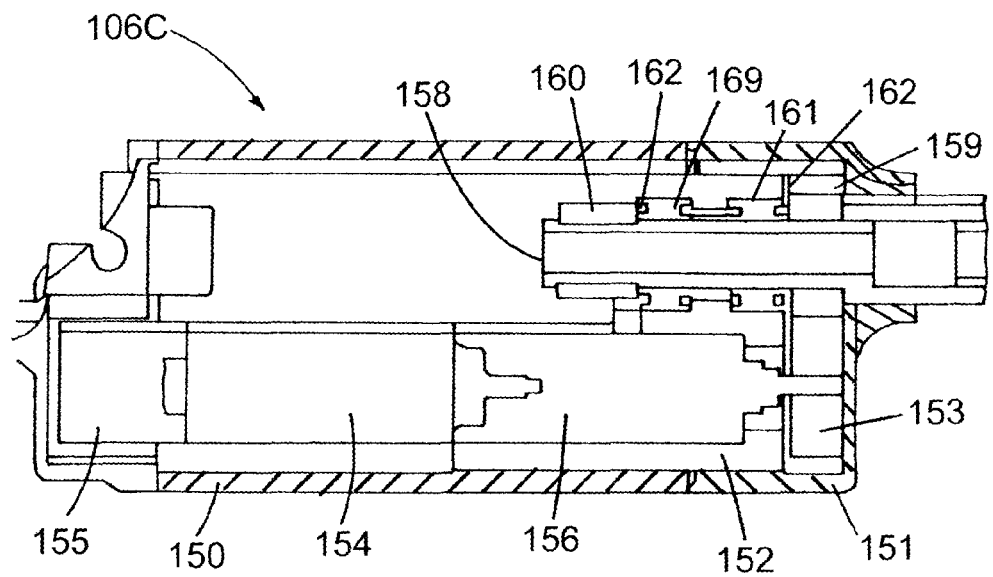
FIG. 3F is a cutaway close-up view of a portion of the device of FIG. 3A.
Figure 3G:
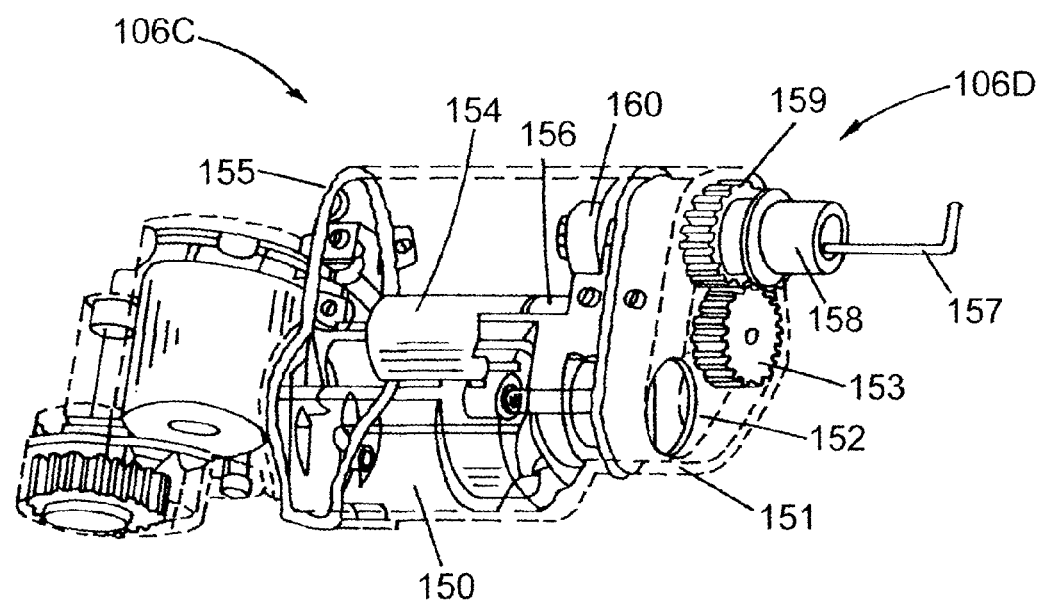
FIG. 3G is a cutaway perspective view of a portion of the device of FIG. 3A.
Figure 3H:
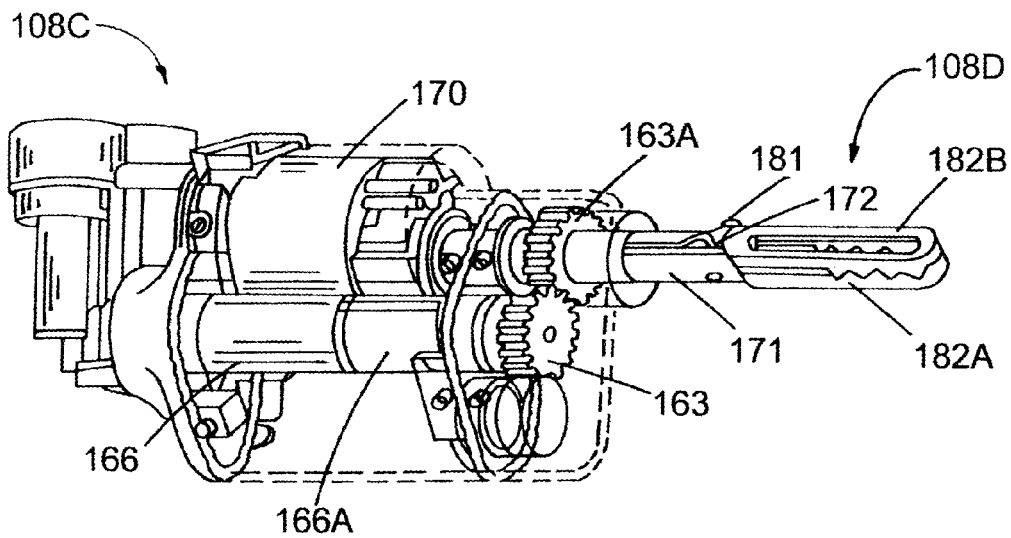
FIG. 3H is a cutaway perspective view of a portion of the device of FIG. 3A.

According to the implementation shown in FIG. 3A, operational component 106D has a cautery tool, and operational component 108D has a grasper. In this embodiment, each of the operational components 106D, 108D is configured to be rotatable around an axis parallel to the longitudinal axis of each of the components 106D, 108D. As best shown in FIGS. 3F and 3G, operational component 106D is a cautery tool comprising a cautery housing 158 and a cautery component 157. Cautery housing 158 and cautery tool 157 are attached to cautery component rotational gear 159, which is rotatably coupled with spur gear 153 housed in third link 106C. The spur gear 153 is actuated by a motor 154 through gearhead 156 coupled to the motor 154. Actuation of the motor 154 and gearhead 156 causes rotation of the spur gear 153, and thus the cautery rotational gear 159, cautery housing 158, and cautery component 157. Encoder 155 provides position information to the interface (not shown) for motor 154. The cautery housing 158 is further coupled to two bearing elements 161, 169 proximal to the cautery rotational gear 159, which support motor housing 152 and reduce rotational friction thereof. Motor housing 152 is further supported by attachment to third link upper housing 150 and third link lower housing 151. The cautery housing 158 and proximal bearing 169 are further coupled to a cautery shaft nut 160 that limits translation of the cautery housing 158 and provides a preload (i.e., a clamping force as a result of tightening the nut) for the two bearing elements 161, 169 to aid in reducing friction during rotation of the cautery shaft. Washer 162 prevents preload nut 160 and cautery rotational gear 159 from contacting ball bearings 161, 169.

Figure 3I:
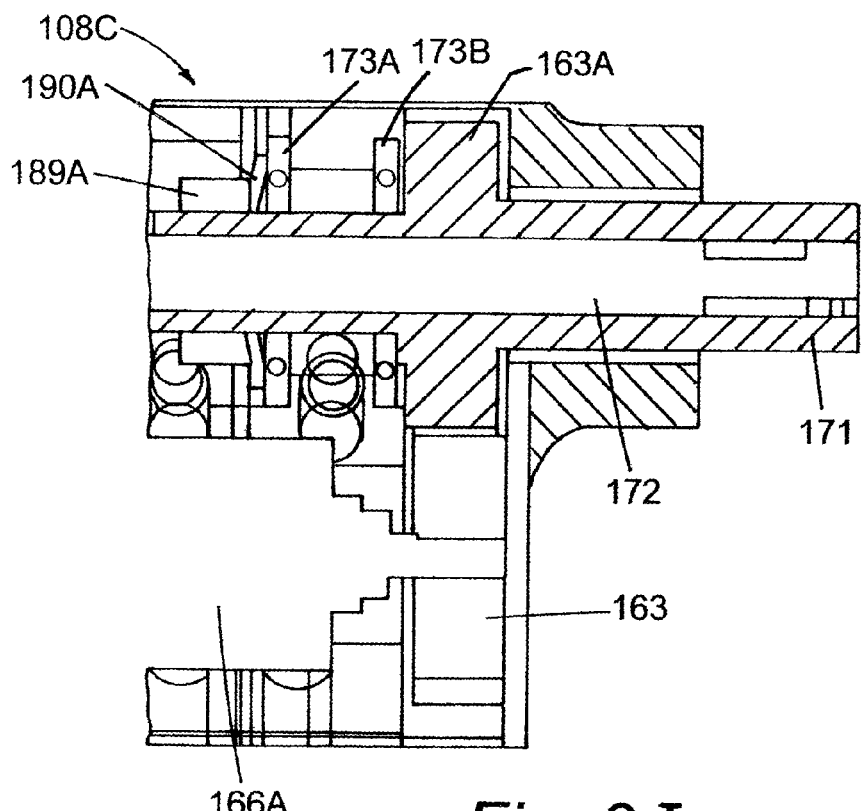
FIG. 3I is a cutaway close-up view of a portion of the device of FIG. 3A.

As best shown in FIGS. 3H-3K, operational component 108D is a grasper tool comprising grasper housing 171, grasper drive pin 172, and grasper jaws 182A, 182B. As best shown in FIG. 3I, grasper housing 171 is attached and rotationally constrained to spur gear 163A, which is rotatably coupled with the spur gear 163 within third link 108C. Actuation of the rotational motor 166 and gearhead 166A causes rotation of the spur gear 163, and thus causes rotation of the grasper housing 171 and operational component 108D. The grasper housing 171 is further coupled to two bearing elements 173A, 173B, which provide support for and reduce rotational friction of the grasper housing 171, distal hex preload nut 189A that limits lateral translation of the grasper housing 171 and provides a preload (i.e., clamping force applied by the nut to reduce friction in the bearings and prevent translation of the bearings) for the bearings 173A, 173B to help reduce friction during rotation of the grasper housing 171. A beveled washer 190A is located between the ball bearing 173B and hex preload nut 189A.

Figure 3J:
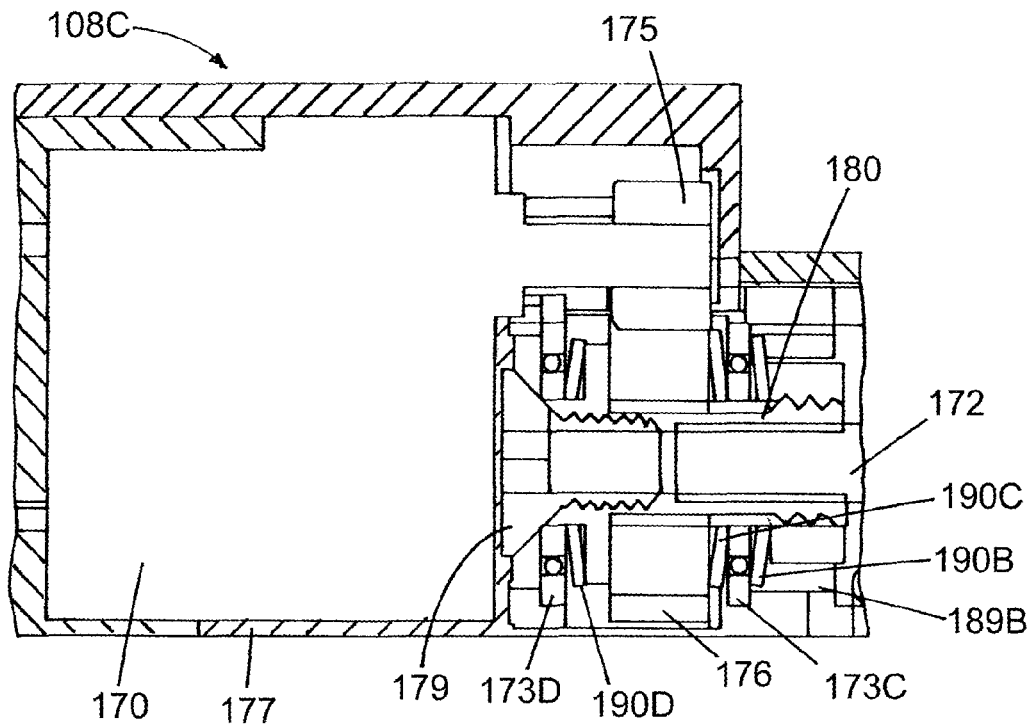
FIG. 3J is a cutaway close-up view of a portion of the device of FIG. 3A.
Figure 3K:
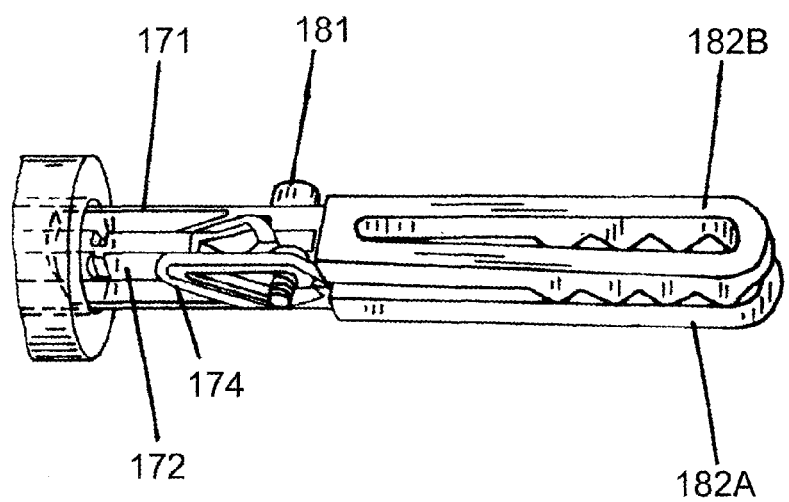
FIG. 3K is a cutaway close-up view of a portion of the device of FIG. 3A.

As best shown in FIG. 3J, motor 170 is rigidly coupled to motor housing 177 using, for example one or more bolts, to constrain the translation and rotation motion of the motor 170 to the motor housing 177. Actuation motor 170 is rigidly coupled to the actuation spur gear 175. Actuation of motor 170 causes rotation of spur gear 175, which translates to rotation of spur gear 176. Spur gear 176 is rigidly coupled to the driveshaft housing 180 which is, in turn, rigidly coupled to the grasper driveshaft 172. Rotation of spur gear 176 via actuation of the motor 170 therefore results in rotation of the driveshaft housing 180 and the translation of the grasper driveshaft 172 due to it being constrained radially by 182A and 182B. Best shown in FIG. 3K, a grasper rotation bolt 181 threads through one side of the grasper housing 171 and goes through a hole in both graspers 182A, 182B. A pin 174 machined into the grasper drive pin 172 rides in grooves of 182A, 182B. As the grasper drive pin 172 is translated, the pin 174 moves along the grooves of 182A and 182B, causing the graspers to open and close. In one embodiment, rotation of the grasper driveshaft 180 is aided by a proximal hex preload nut 189B, beveled washers 190B 190C, 190D and bearing elements 173C, 173D. The driveshaft housing 180 is further rigidly coupled to a driveshaft housing screw 179 that constrains translation of the driveshaft housing 180 to the proximal bearing 173D.

According to one embodiment, each operational component 106D, 108D can have two tools with each of the operational components 106D, 108D being configured to be rotatable around an axis parallel to the longitudinal axis of each of the components 106D, 108D. For example, in one embodiment, each operational component 106D, 108D has two configurations—a grasper configuration and a cautery tool configuration. In the grasper configuration, the operational component 106D, 108D has been rotated such that the grasper is positioned substantially along the longitudinal axis of the third link 106D, 108D and thus is operational. In contrast, in the cautery tool configuration, the operational component 106D, 108D has been rotated such that the cautery tool is positioned substantially along the longitudinal axis of the third link 106D, 108D and thus is operational. In this embodiment, each of the two tools can be configured to operate similarly to the embodiments with a single tool at operational components 106D, 108D above.

It is understood that operational components 106D, 108D are completely independent such that the two configurations of each such component 106D, 108D are independent as well. That is, while the operational component of one arm is in the grasper configuration, the operational component of the other arm can be in either configuration, and vice versa. Other operational components may also be substituted, as described herein.

In this embodiment, the body 102 is made up of two cylindrical components 102A, 102B that are coupled together, as described above. Alternatively, the body 102 can be a single component and further can be any of the device body embodiments disclosed in the various patent applications incorporated by reference above and elsewhere herein.

Figure 4A:
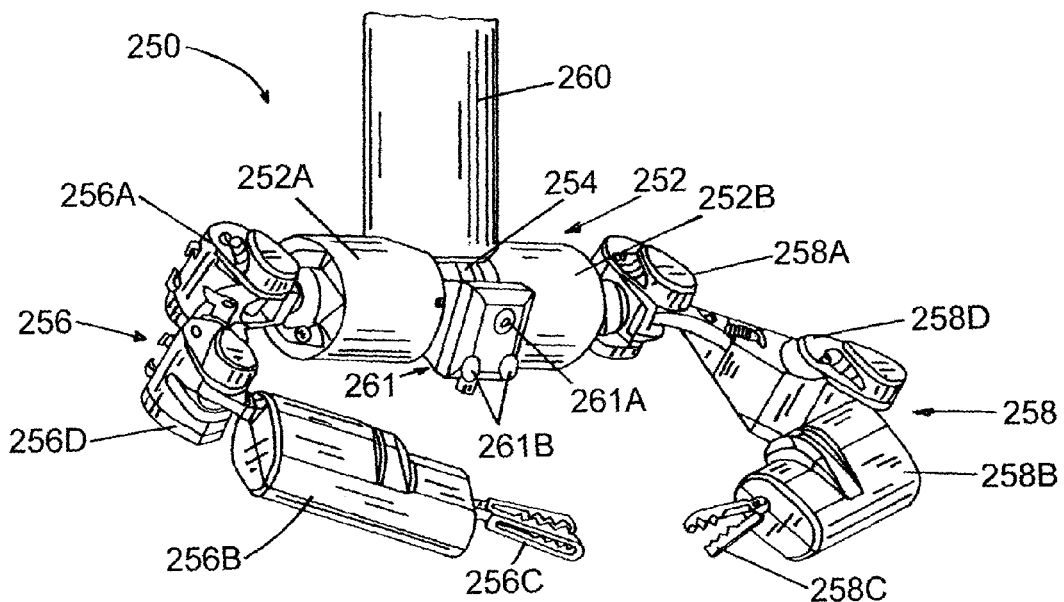
FIG. 4A is a perspective view of a modular medical device, according to another embodiment.
Figure 4B:
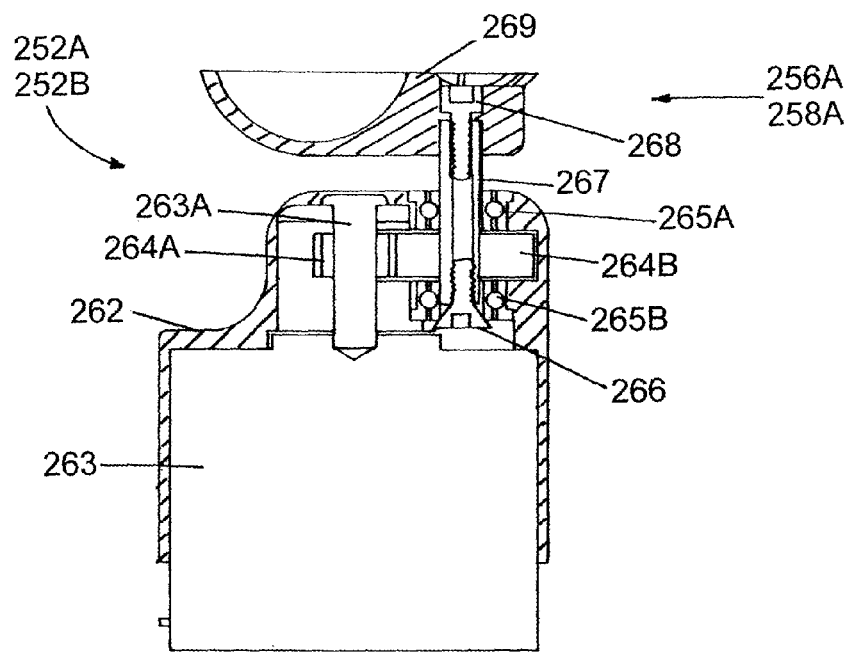
FIG. 4B is a cutaway close-up view of a portion of the device of FIG. 4A.
Figure 4C:
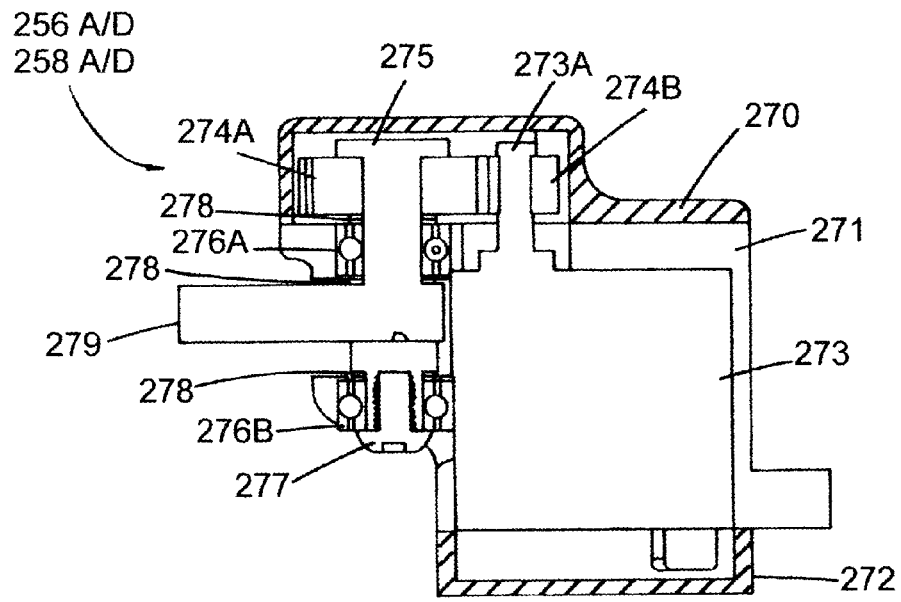
FIG. 4C is a cutaway close-up view of a portion of the device of FIG. 4A.
Figure 4D:
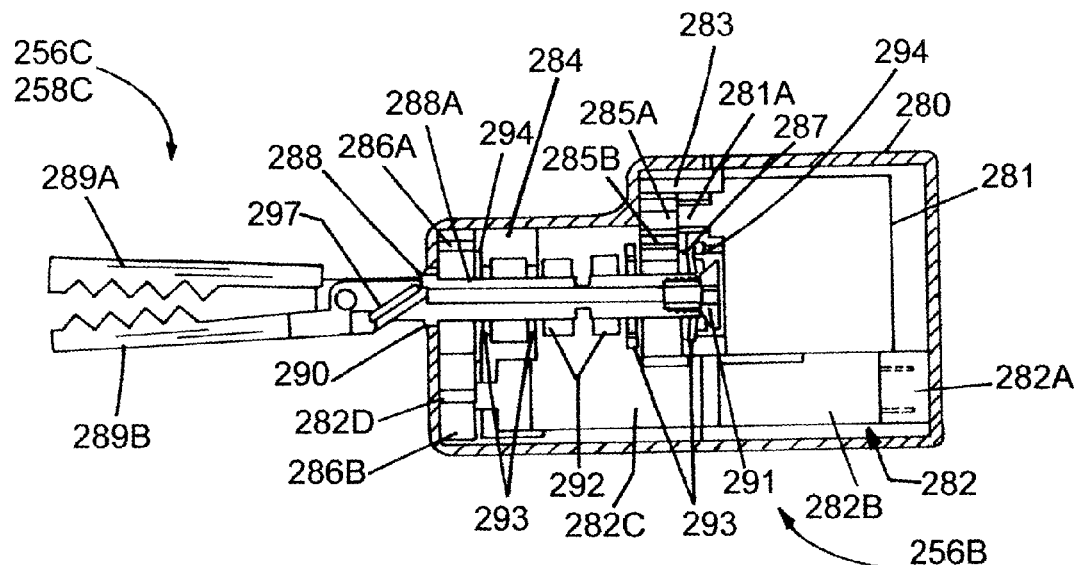
FIG. 4D is a cutaway close-up view of a portion of the device of FIG. 4A.
Figure 4E:
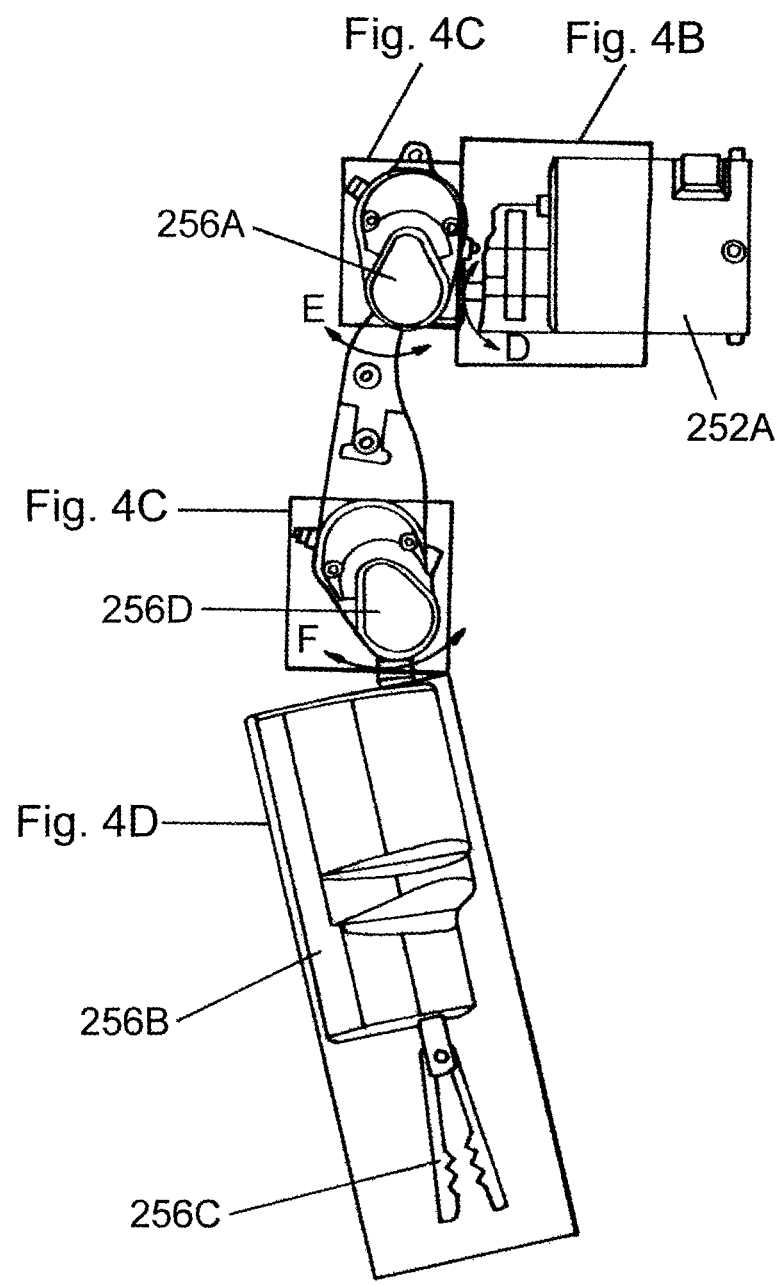
FIG. 4E is a perspective view of a portion of the device of FIG. 4A.
Figure 4F:
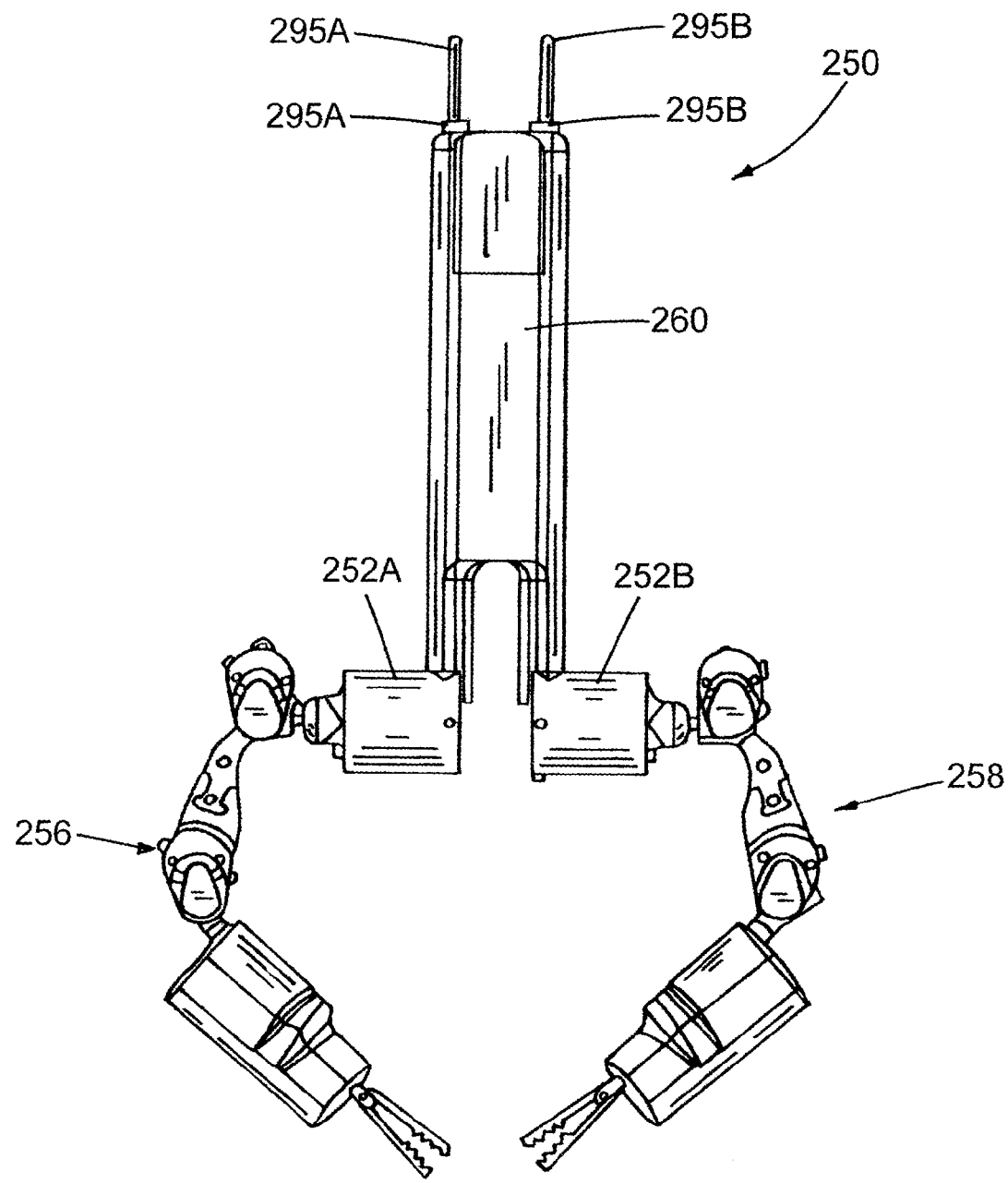
FIG. 4F is a perspective view of a modular medical device, according to another embodiment.

FIGS. 4A-4F depict another embodiment of a robotic medical device 250. As best shown in FIGS. 4A and 4F, device embodiment 250 includes a body 252 having two cylindrical components 252A, 252B that are coupled to each other at a connection point 254. The device has two arms 256, 258 that are coupled to the body 252. More specifically, the first arm 256 is rotatably coupled to the first cylindrical component 252A and the second arm 258 is rotatably coupled to the second cylindrical component 252B. The first arm 256 has a first link 256A that is coupled to the first component 252A, a second link 256D that is coupled to the first link 256A, and a third link 256B that is coupled to second link 256D. Similarly, the second arm 258 has a first link 258A that is coupled to the second component 252B, a second link 258D that is coupled to the first link 258A, and a third link 258B that is coupled to second link 258D. The first arm 256 has an operational component 256C coupled to the third link 256B, and the second arm 258 has an operational component 258C coupled to the third link 258B. FIG. 4F is an image of device 250 with support rod attached. Each body component 252A, 252B is connected to a control rod 295A, 295B. The control rods 295A, 295B can be used to manipulate the position of the device 250 during insertion into the body. Once the device 250 is positioned, a custom mating support rod 260 can be introduced. Once mated, the support rod 260 constrains gross position of the arms 256, 258 with respect to each other. The support rod 260 is constrained to the control rods 295A, 295B by nuts 296A, 296B on the top and a specific mating geometry on the bottom. In some embodiments, as best shown in FIG. 4A, device 250 includes vision system 261. Vision system 261 can include a small camera 261A and ultra-bright light emitting diodes 261B.

As best shown in FIG. 4E, the first link 256A is coupled to the first component 252A such that the first link 256A can rotate around an axis parallel to the longitudinal axis of the first component 252A. In addition, the first link 256A can also rotate in direction D around an axis perpendicular to the longitudinal axis of the first component 252A. Similarly, the first link 258A is coupled to the second component 252B such that the first link can rotate around an axis parallel to the longitudinal axis of the second component 252B. In addition, the first link 258A can also rotate around an axis perpendicular to the longitudinal axis of the second component 252B. The second link 256D is coupled to the first link 256A such that the second link 256D can rotate in direction E around an axis perpendicular to the longitudinal axis of the first link 256A. Similarly, the second link 258D is coupled to the first link 258A such that the second link 258D can rotate around an axis perpendicular to the longitudinal axis of the first link 258A. The third link 256B is coupled to the second link 256D such that the third link 256B can rotate in direction F around an axis perpendicular to the longitudinal axis of the second link 256D. Similarly, third link 258B is coupled to the second link 258D such that the third link 258B can rotate around an axis perpendicular to the longitudinal axis of the second link 258D. Operational component 256C is coupled to the third link 256B such that the operational component 256C can rotate around an axis parallel to the longitudinal axis of the third link 256B. Similarly, operational component 258C is coupled to the third link 258B such that the operational component 258C can rotate around an axis parallel to the longitudinal axis of the third link 258B.

First component 252A, as best shown in FIG. 4B, comprises a torso motor housing 262 that holds the motor 263 and actuation mechanism. The actuation mechanism includes a spur gear 264A rigidly attached to the output shaft 263A of the motor 263. As the motor output shaft 263A turns, spur gear 264A rotates spur gear 264B, which is radially constrained with the torso rotational shaft 267 by a flat placed on both spur gear 264B and shaft 267. The rotational shaft 267 is supported with two flanged ball bearings 265A, 265B. The torso rotational shaft 267 is constrained to the first link 256A by a screw 268. Shaft 267 is also axially constrained to the first link 256A by screw 266. Second component 252B is similarly configured to first component 252A.

First link 256A, as best shown in FIG. 4C, comprises an upper arm motor housing 271 that holds the motor 273 and actuation mechanism. The actuation mechanism includes a spur gear 274B rigidly attached to the output shaft 273A of the motor 273. As the motor output shaft 273A turns, spur gear 274B rotates spur gear 274A, which is radially constrained with the output rotational shaft 275 by a flat placed on both spur gear 274A and shaft 275. The output rotational shaft 275 is supported with two ball bearings 276A, 276B. The output rotational shaft 275 is constrained to the output link 279 by a flat placed on both shaft 275 and output link 279. Output rotational shaft 275 is also axially constrained by a screw 277. Washers 278 are used to maintain spacing and to preload the bearings. A gear cap 270 and a wiring cap 272 connect to the motor housing 271. First link 258A and second links 256D, 258D are configured similarly to first link 256A.

Third link 256B, as best shown in FIG. 4D, comprises a forearm body 280 that is made of two symmetric halves that mate. Third link 256B additionally comprises components for rotating operational component 256C around an axis parallel to the longitudinal axis of the third link 256B. Operational component 256 rotation is accomplished using motor system 282. Motor system 282 comprises motor 282B connected to encoder 282A, which provides position information to the interface (not shown) for motor 282B, and planetary gearhead 282C. Motor system 282 is seated within a forward forearm housing 284 that provides appropriate spacing. Spur gear 286B is rigidly attached to the output shaft 282D of the gearhead 282C. As the gearhead output shaft 282D turns, spur gear 286B rotates spur gear 286A, which is radially constrained by epoxy with the output rotational shaft 288. The output rotational shaft 288 is supported with two thin ball bearings 293. Beveled washers 294 are used to maintain spacing and to preload the bearings. A preload nut 292 is used to axially constrain everything on the output shaft.

Figure 4G:
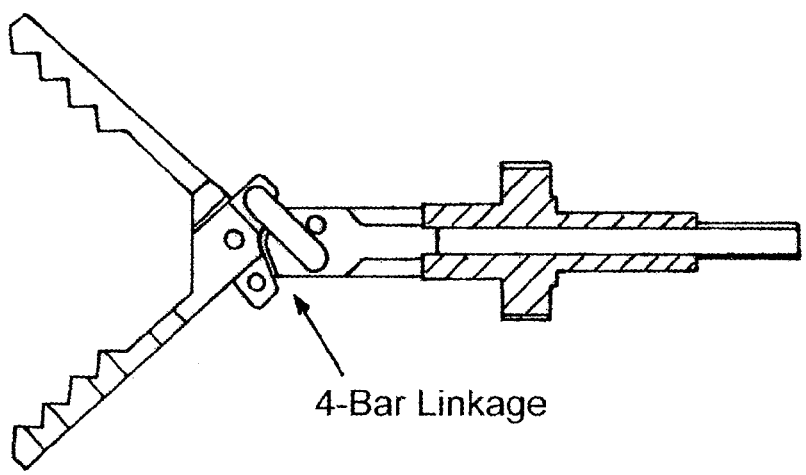
FIG. 4G is a close-up view of a modular medical device according to another embodiment.
Figure 4G:
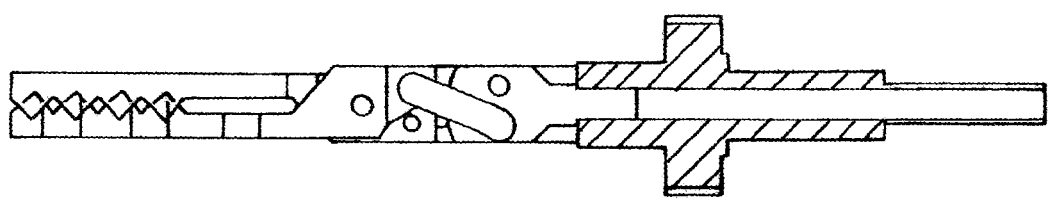

As best shown in FIG. 4D, third link 256B also comprises components for opening and closing grasping jaws 289A, 289B. The actuation mechanism for opening and closing jaws 289A, 289B includes motor 281, which is seated within a rear forearm housing 283 that keeps proper spacing between all parts. Spur gear 285A is rigidly attached to the output shaft 281A of the motor 281. As the motor output shaft turns, spur gear 285A rotates spur gear 285B, which is radially constrained with pressed pins to the rear output shaft 287. The rear output shaft 287 is supported with two thin ball bearings 293. Beveled washers 294 are used to maintain spacing and to preload the bearings. A preload nut 292 and a screw 291 are used to axially constrain everything on the rear output shaft 287. In order to open/close the jaws 289A, 289B, a drive rod 290 is translated linearly using a screw connection between drive rod 290 and rear output shaft 287. As rear output shaft 287 rotates, the screw interface between rear output shaft 287 and drive rod 290 causes the drive rod 290 to translate within the inner opening 288A of the output rotational shaft 288. Two angled slots 297, one on each of the grippers 289A, 289B, are mated as a sliding fit to a pin in the drive rod 290 to cause the jaws 289A, 289B to open or close as drive rod 290 is translated linearly. Alternatively, as best shown in FIG. 4G, actuation of jaws 289A, 289B can be done using a four bar mechanism. Third link 258B is configured similarly to third link 256B.

Figure 5A:
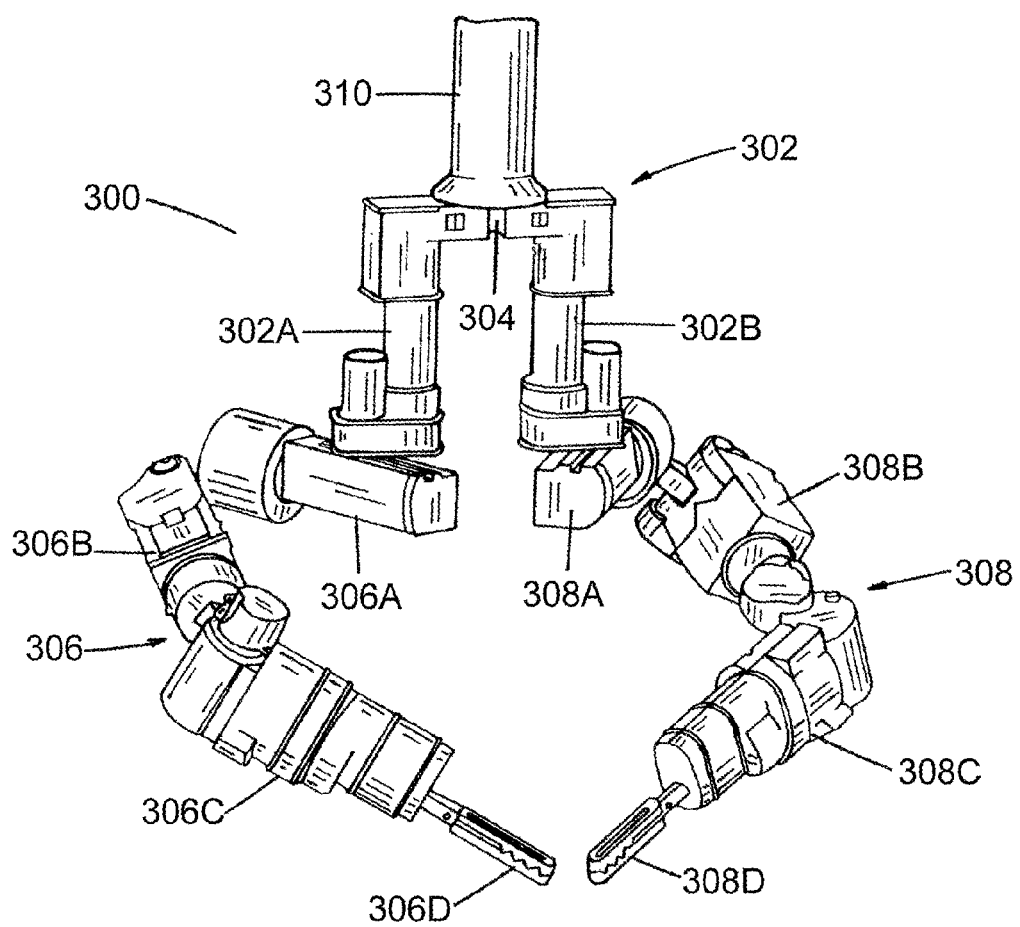
FIG. 5A is a perspective view of a modular medical device, according to another embodiment.
Figure 5B:
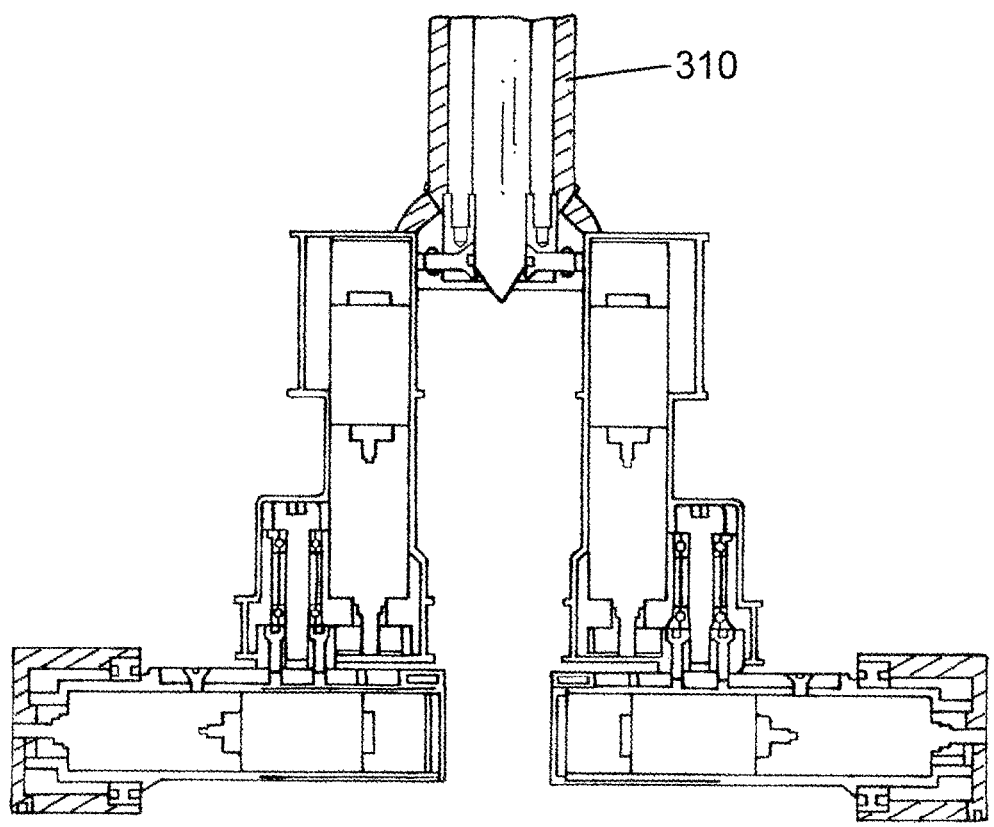
FIG. 5B is a cutaway close-up front view of a portion of the device of FIG. 5A.
Figure 5C:
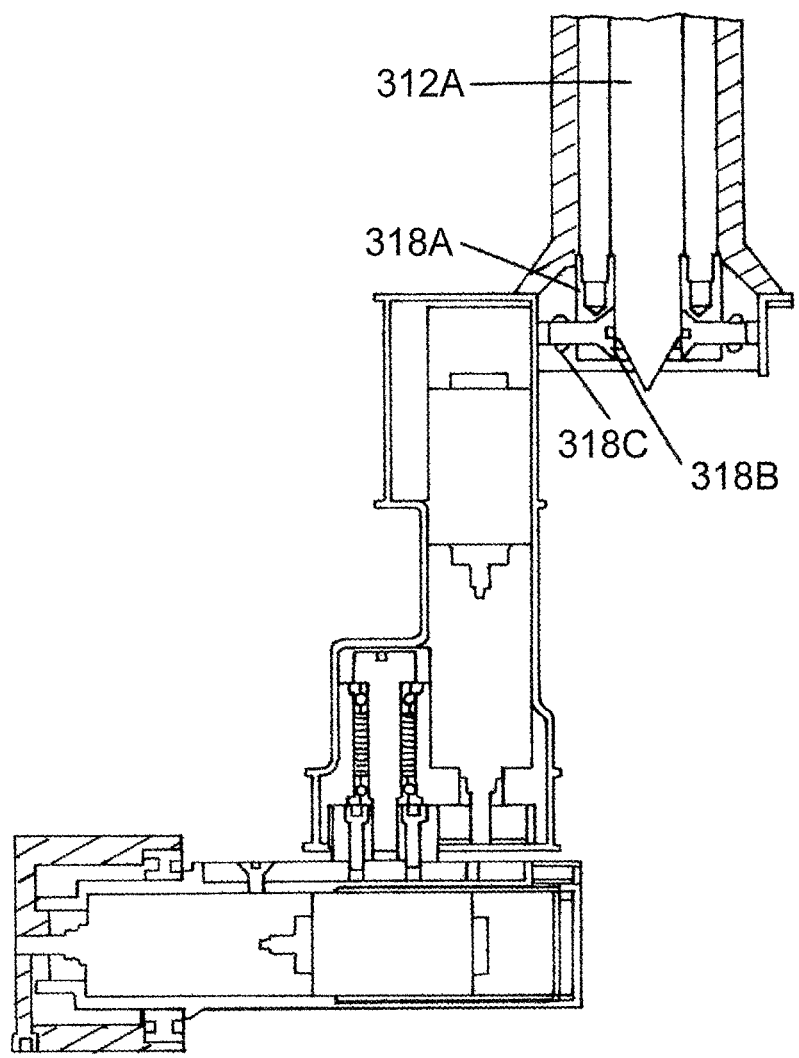
FIG. 5C is a cutaway close-up front view of a portion of the device of FIG. 5A.
Figure 5D:
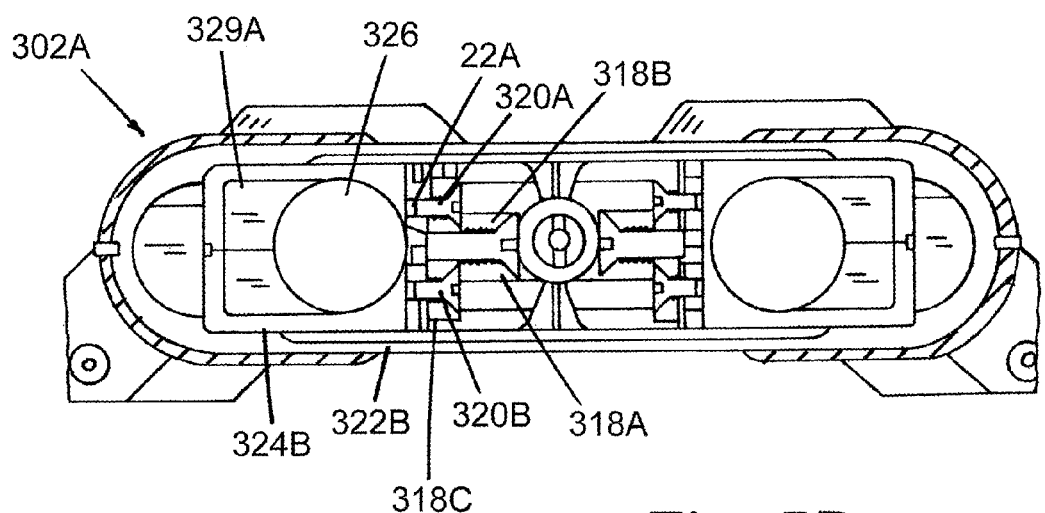
FIG. 5D is a cutaway top view of a portion of the device of FIG. 5A.
Figure 5E:
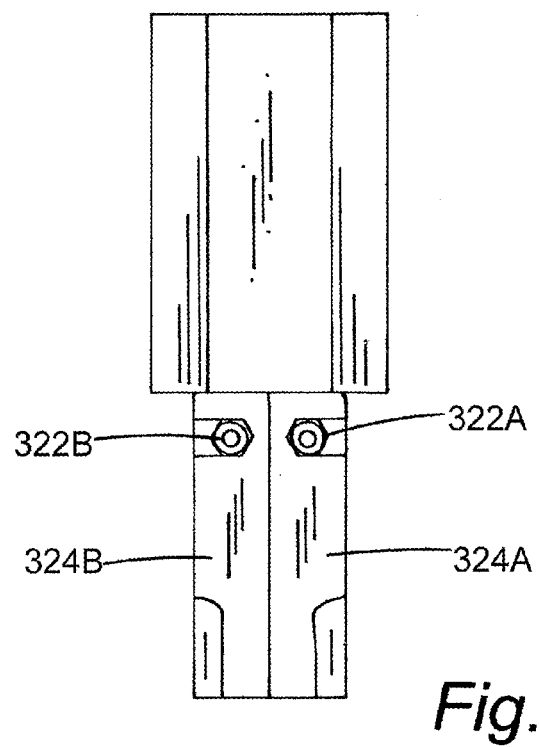
FIG. 5E is a perspective close-up view of a portion of the device of FIG. 5A.
Figure 5F:
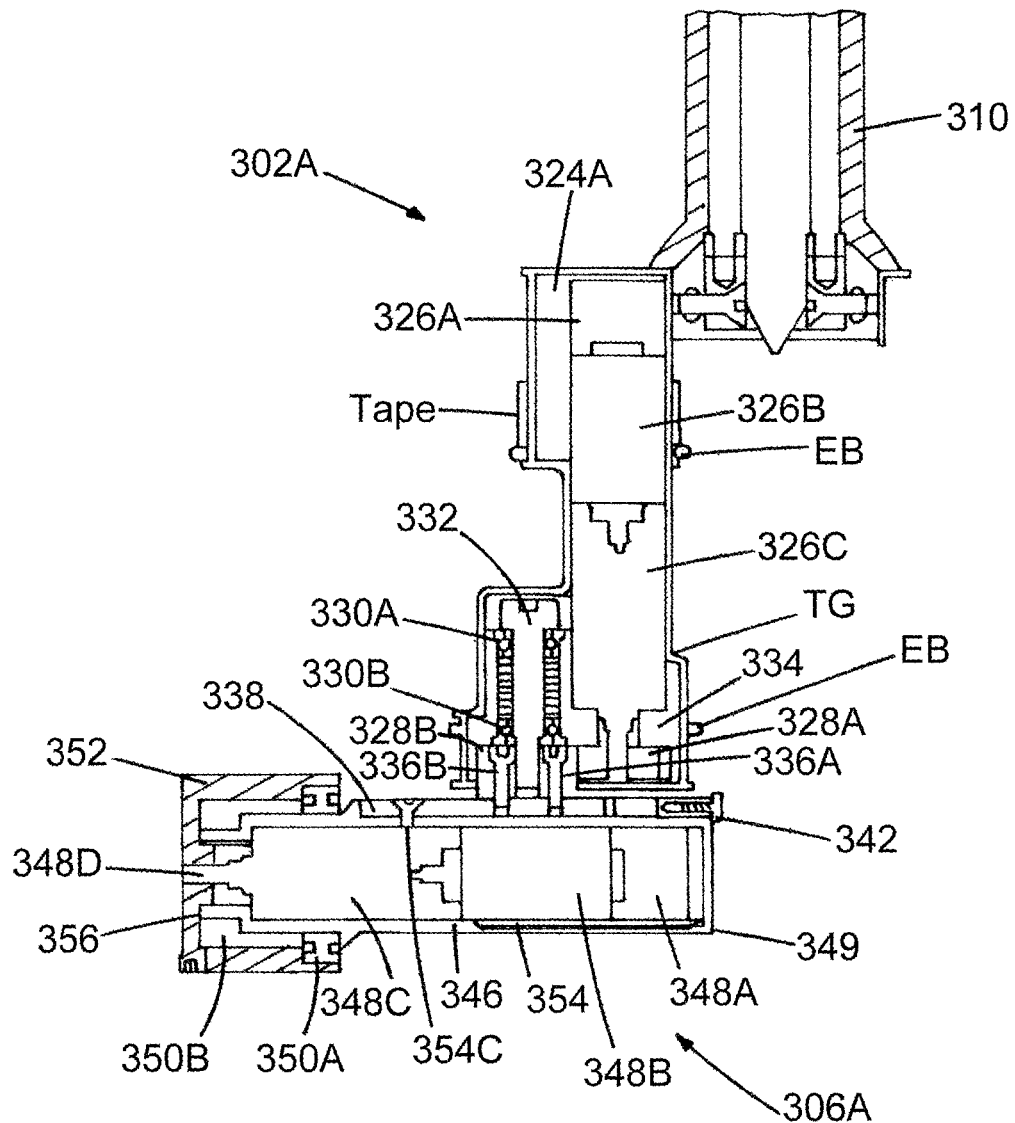
FIG. 5F is a cutaway close-up front view of a portion of the device of FIG. 5A.
Figure 5G:
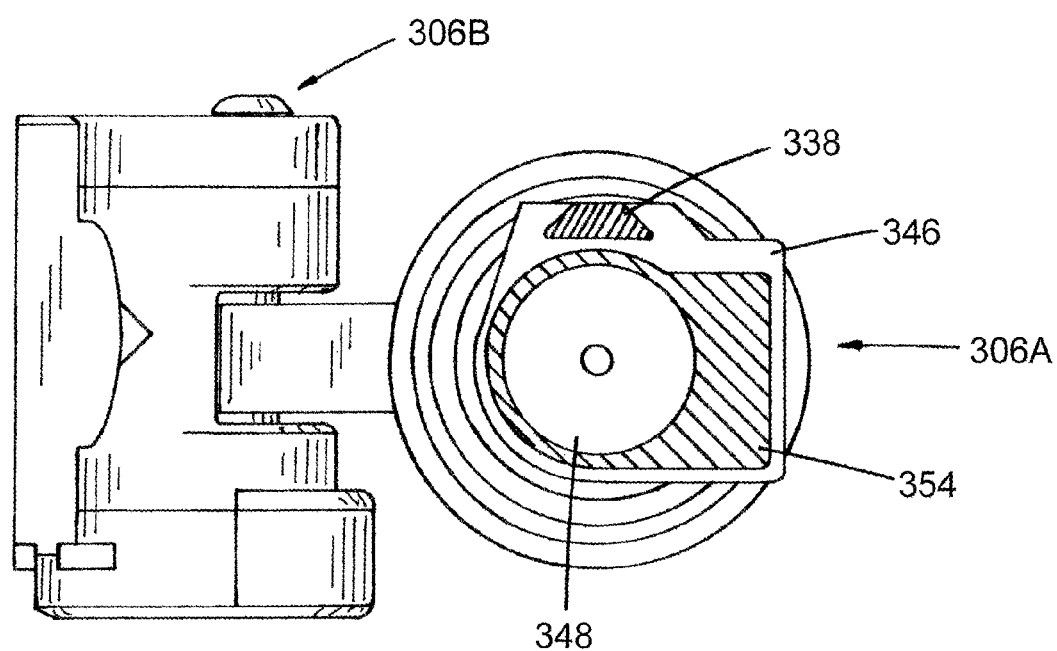
FIG. 5G is a cutaway close-up side view of a portion of the device of FIG. 5A.
Figure 5H:
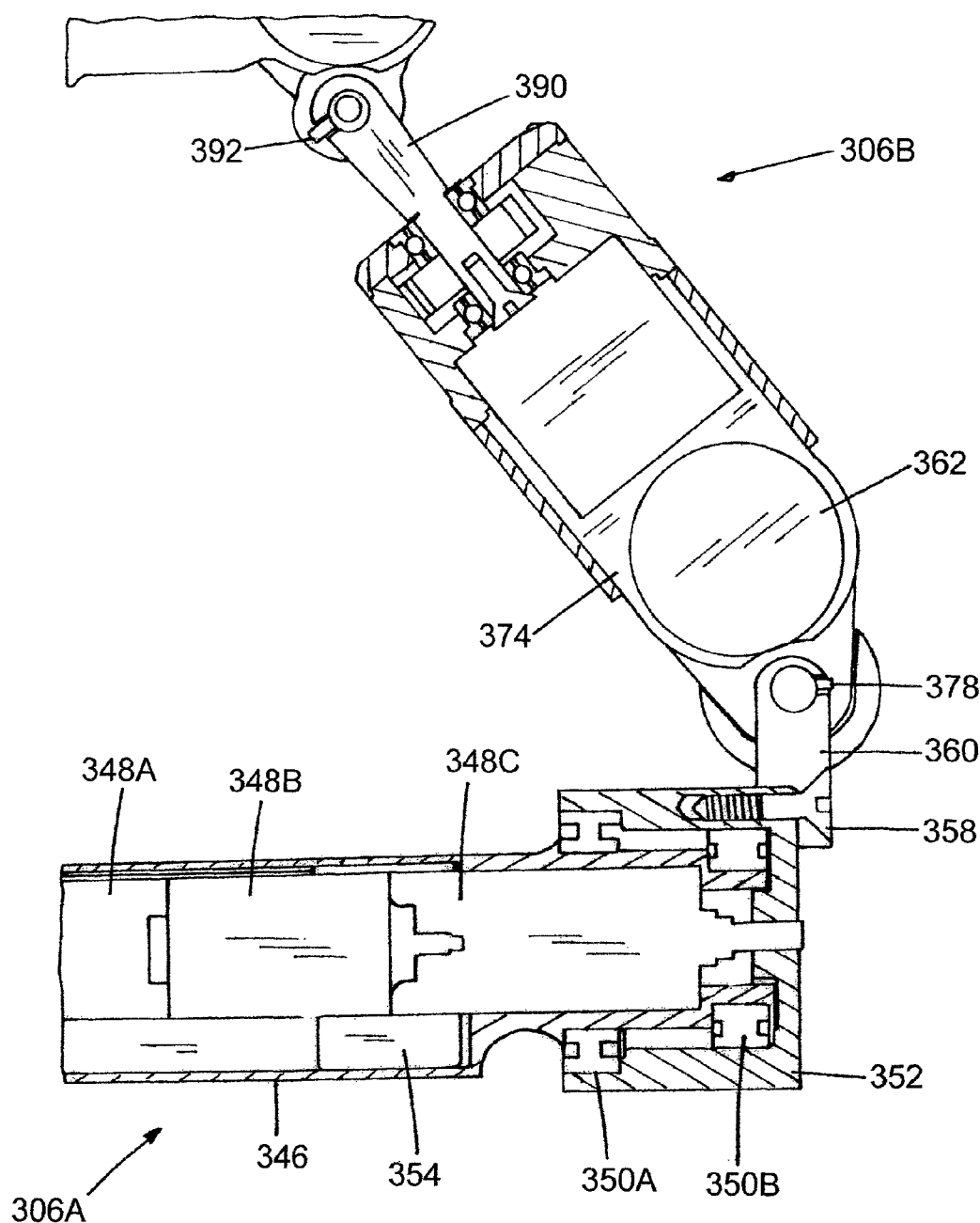
FIG. 5H is a cutaway close-up top view of a portion of the device of FIG. 5A.
Figure 5I:
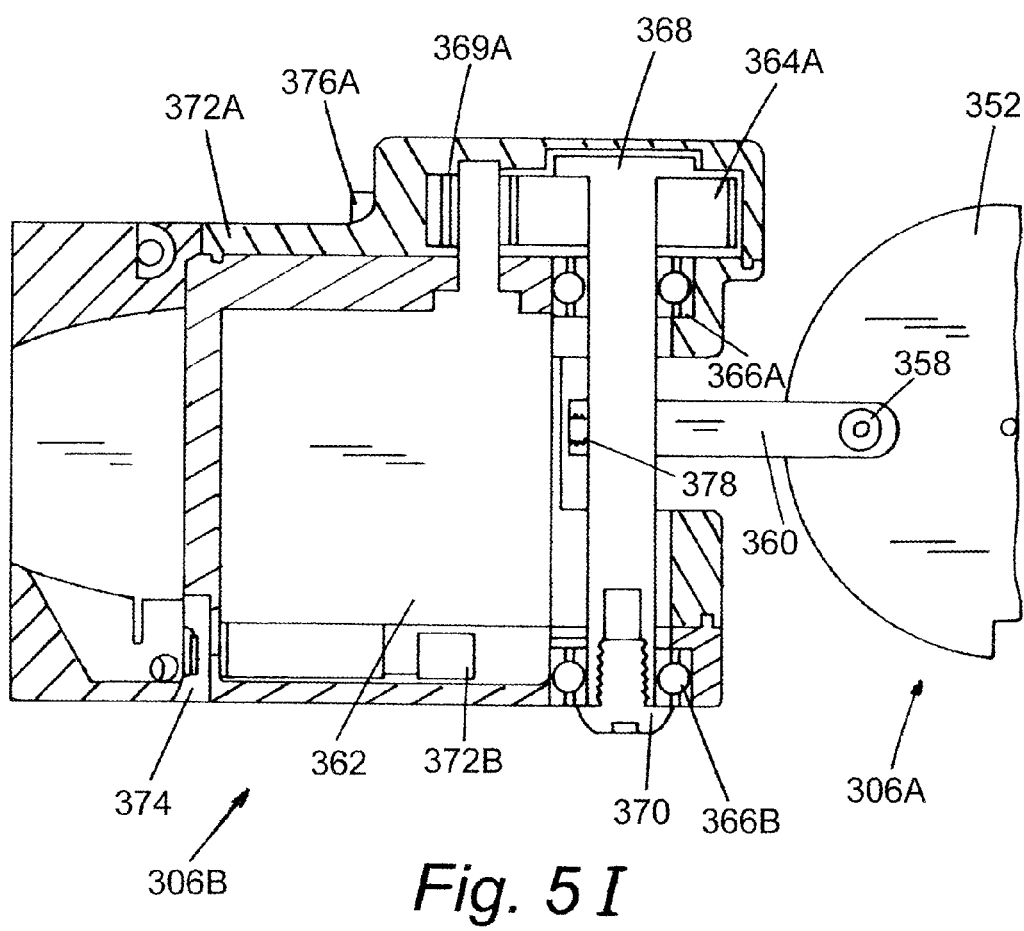
FIG. 5I is a cutaway close-up side view of a portion of the device of FIG. 5A.
Figure 5K:
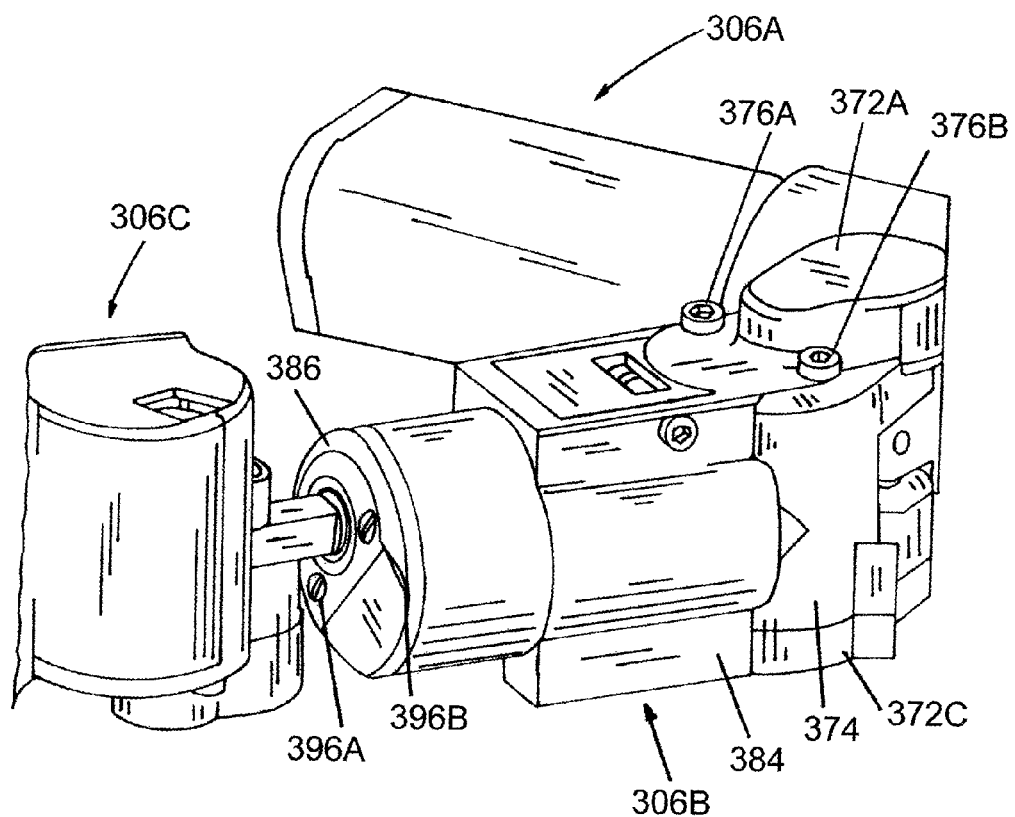
FIG. 5K is a bottom isometric close-up view of a portion of the device of FIG. 5A.
Figure 5L:
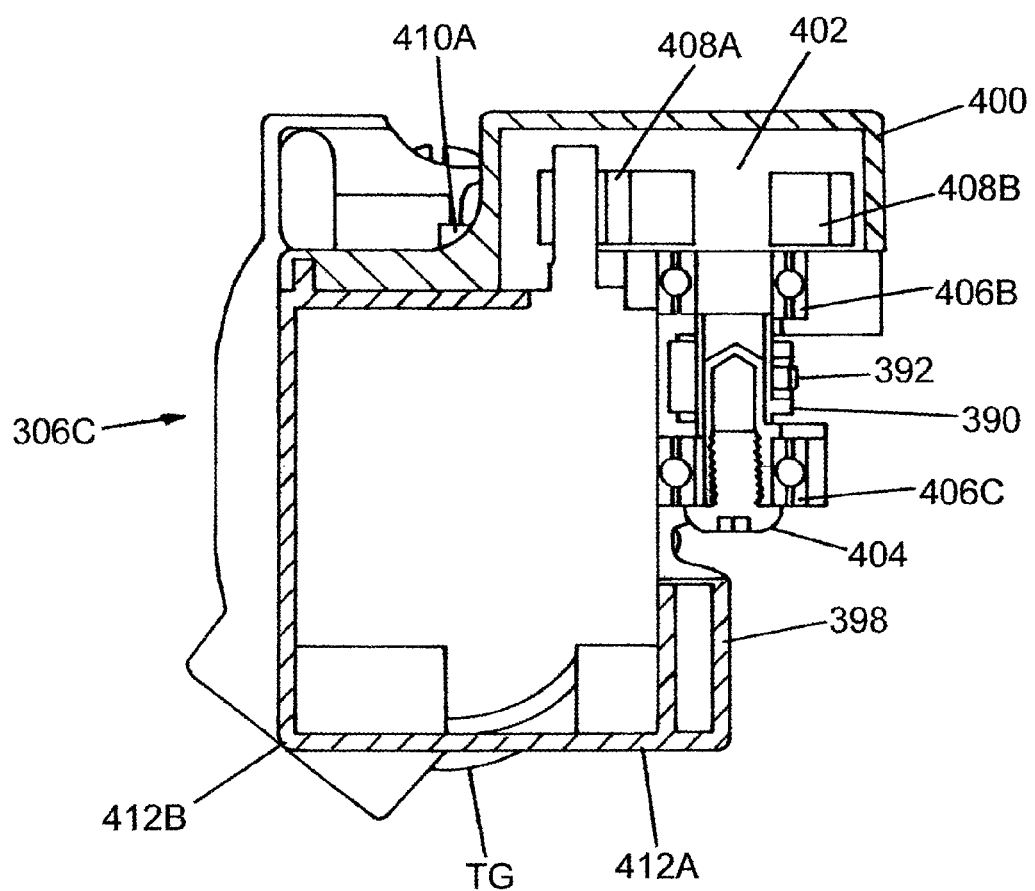
FIG. 5L is a cutaway close-up view of a portion of the device of FIG. 5A.
Figure 5M:
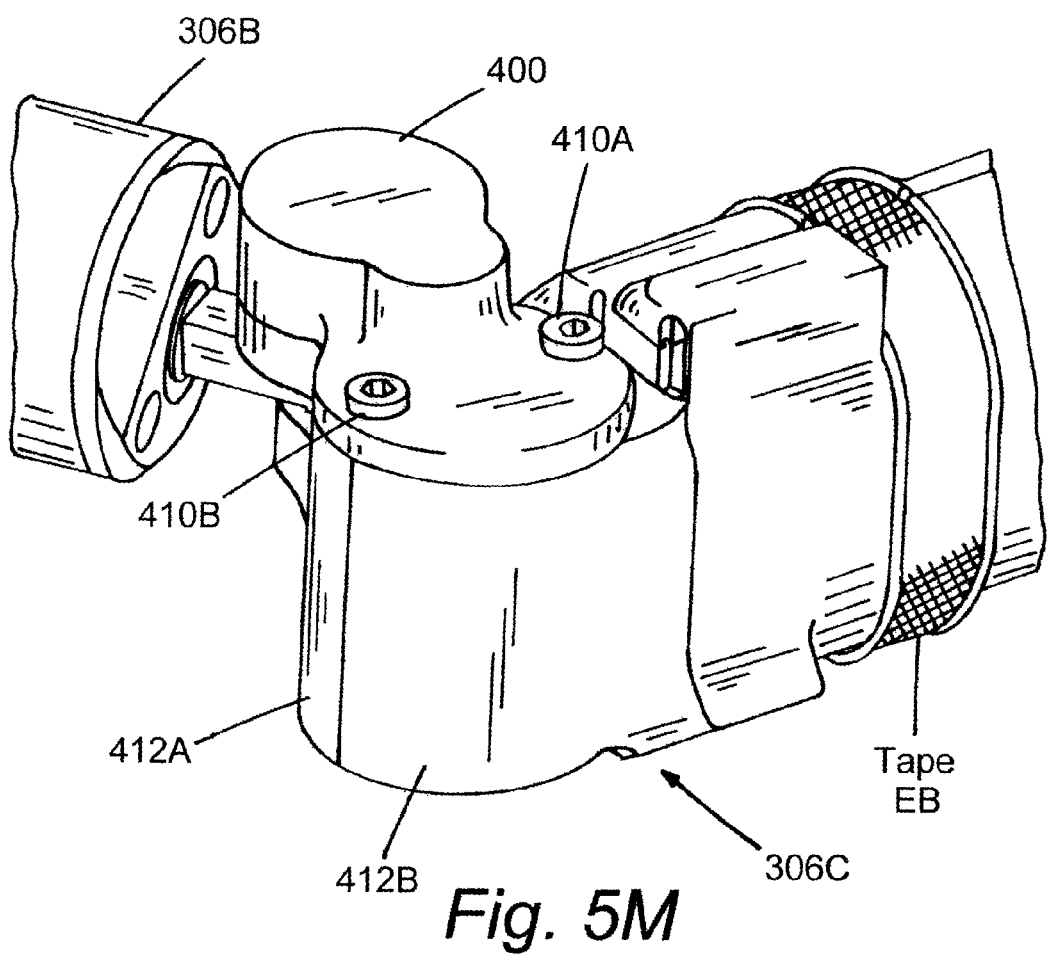
FIG. 5M is a perspective close-up view of a portion of the device of FIG. 5A.
Figure 5N:
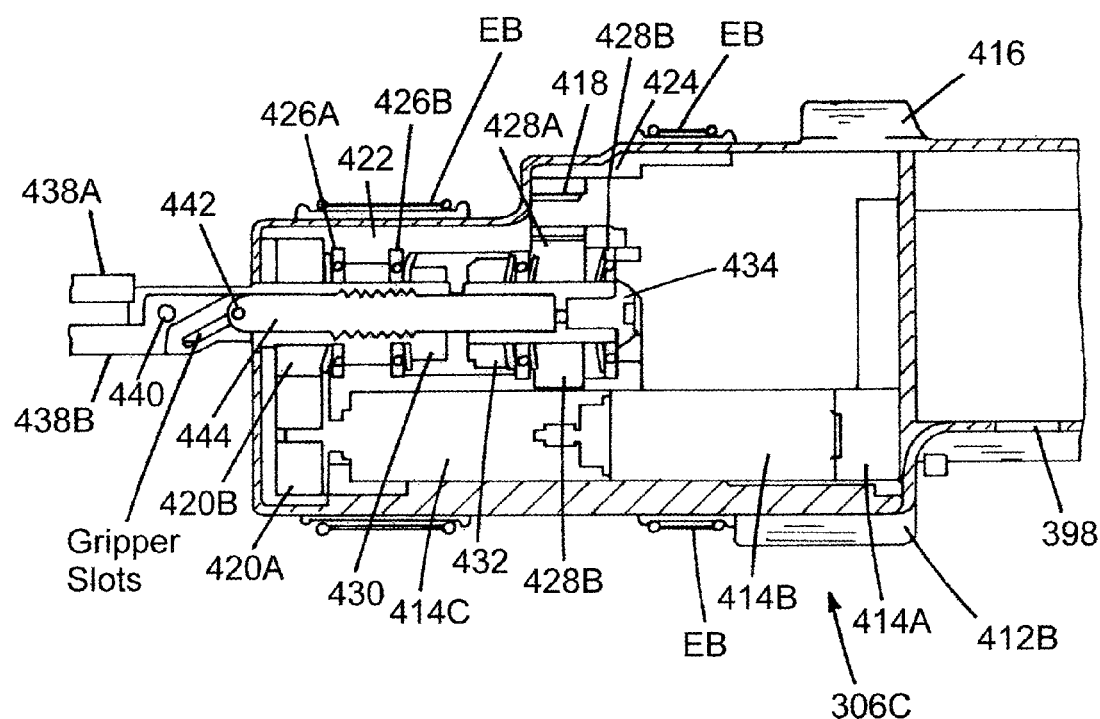
FIG. 5N is a cutaway close-up side view of a portion of the device of FIG. 5A.
Figure 5:
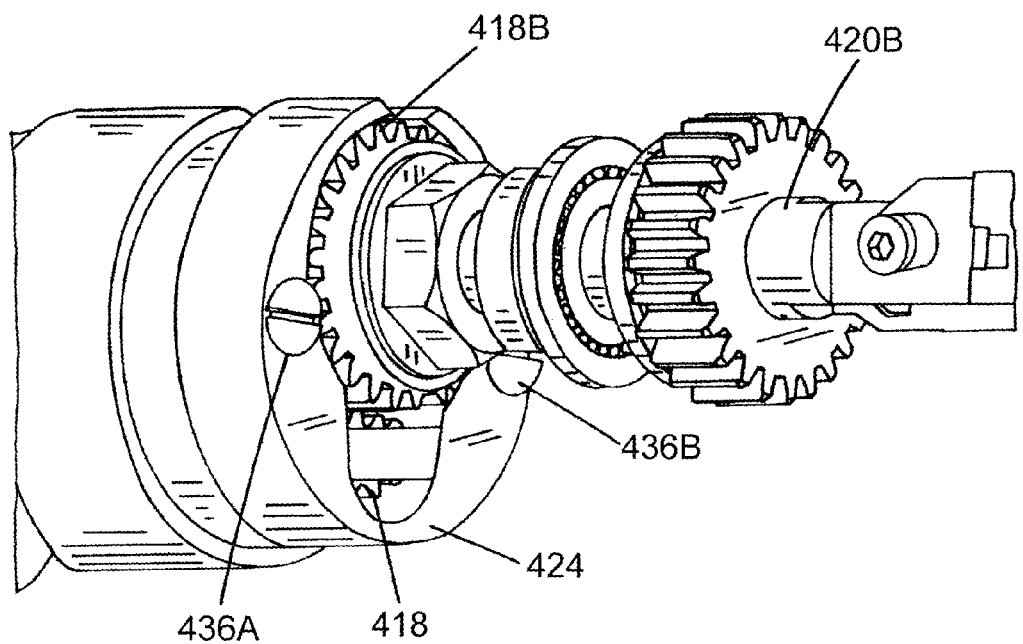
FIG. 5J is a cutaway close-up side view of a portion of the device of FIG. 5A.
FIG. 5O is an isometric interior close-up view of a portion of the device of FIG. 5A.
FIG. 5P is an isometric interior close-up view of a portion of the device of FIG. 5A.
FIG. 5Q is an isometric interior close-up view of a portion of the device of FIG. 5A.
FIG. 5R is an isometric view of a portion of the device of FIG. 5A in one position.
FIG. 5S is an isometric view of a portion of the device of FIG. 5A in another position.
Figure 5P:
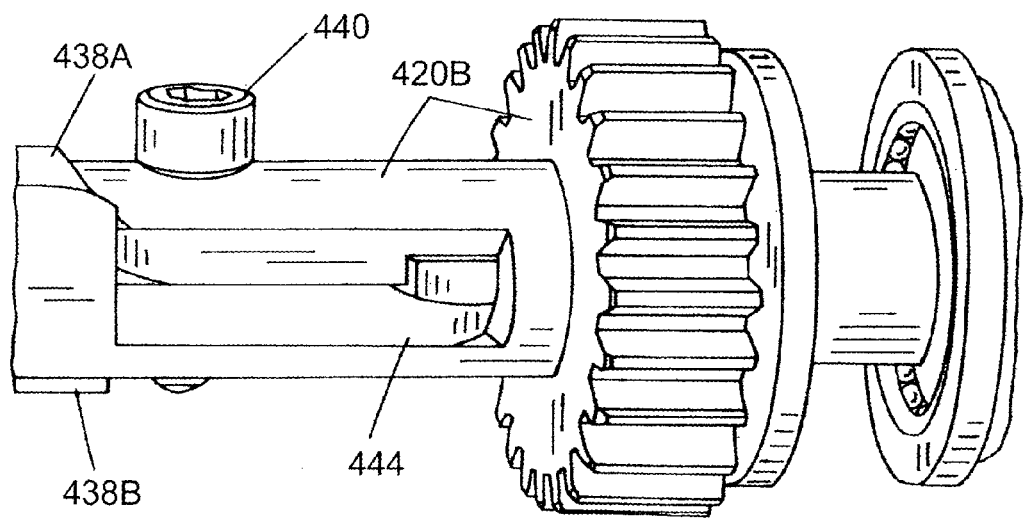
Figure 5Q:
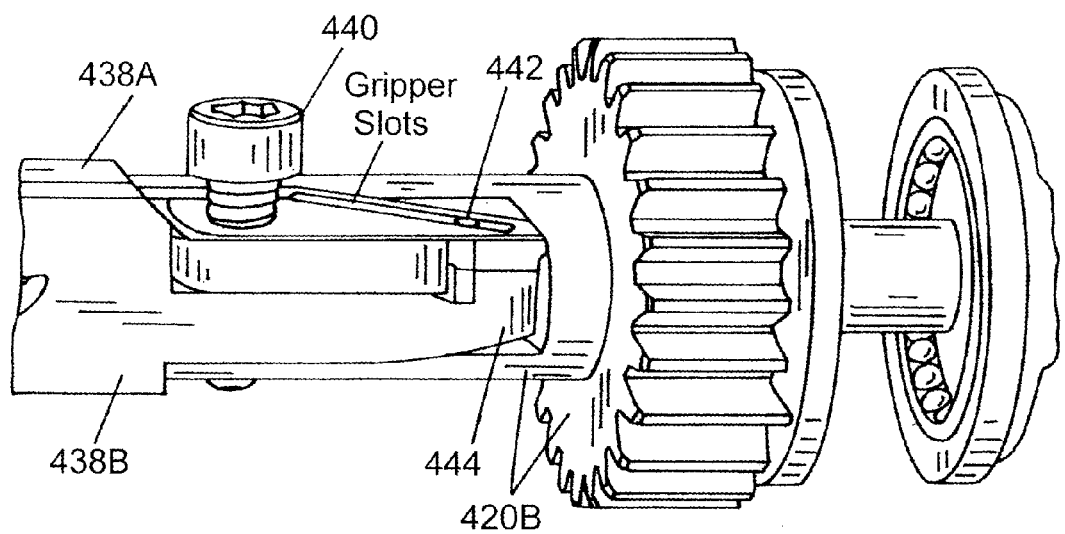
Figure 5R:
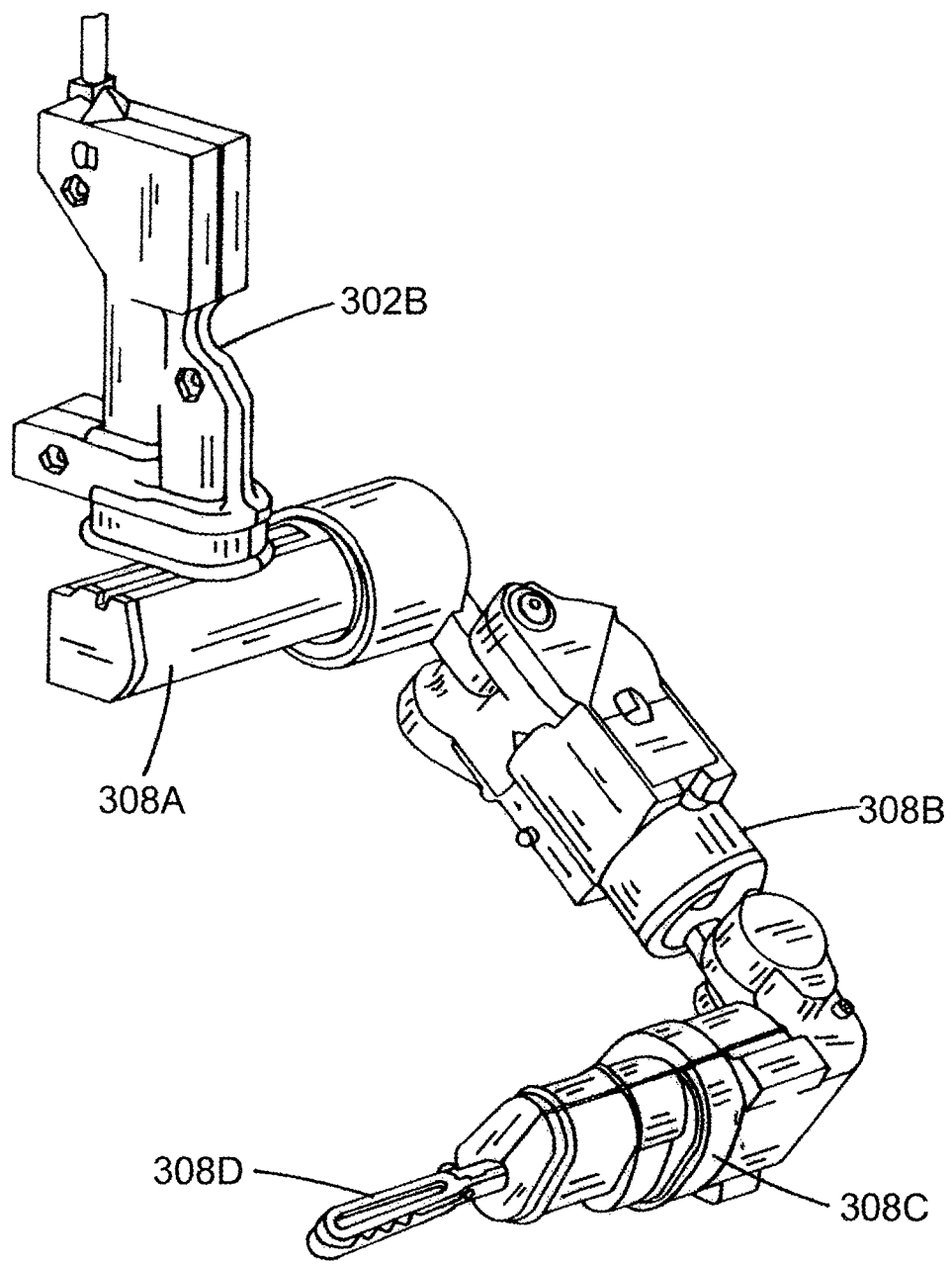
Figure 5S:
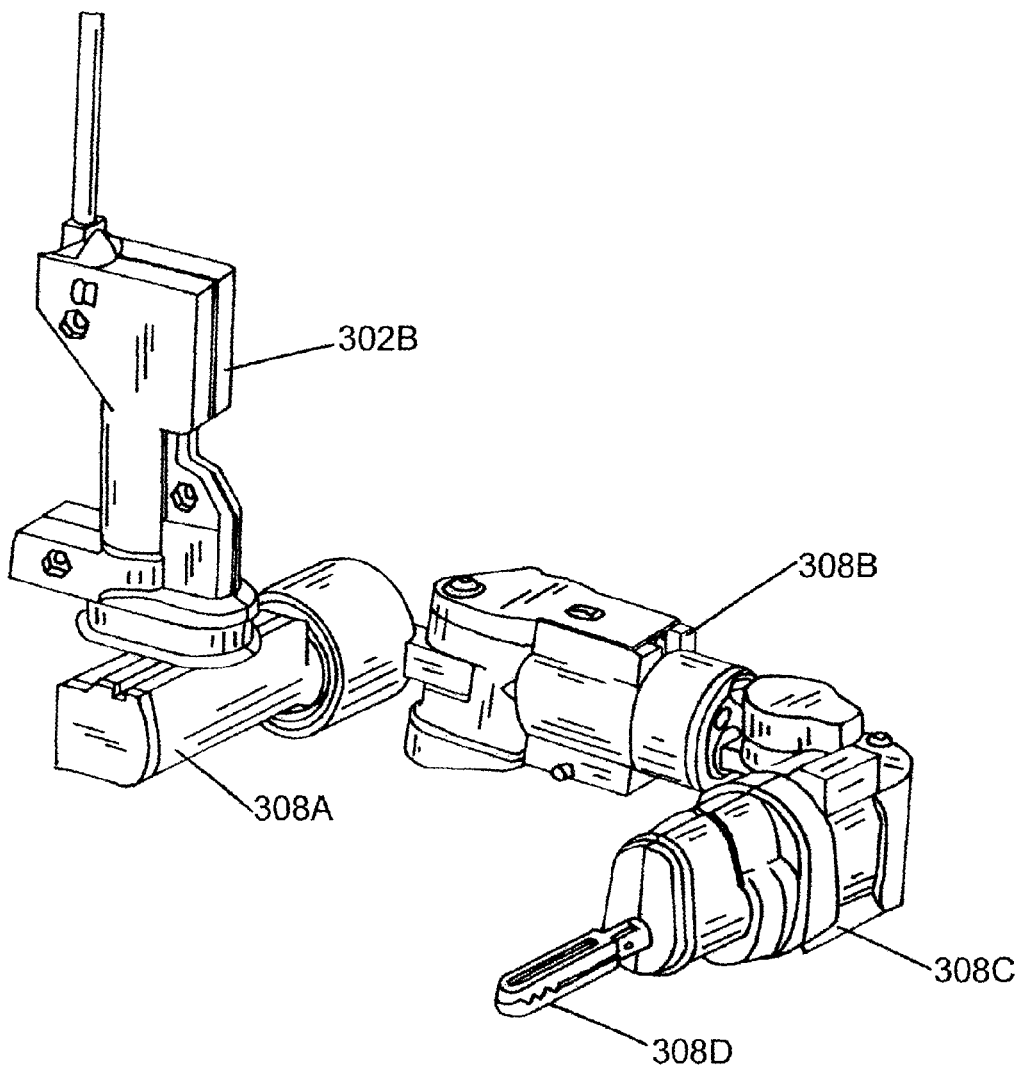

FIGS. 5A-5S depict another embodiment of a robotic medical device 300. This device embodiment 300 as shown includes a body 302 having two cylindrical components 302A, 302B that are coupled to each other at a connection point 304. The device has two arms 306, 308 that are coupled to the body 302. More specifically, the first arm 306 is rotatably coupled to the first cylindrical component 302A and the second arm 308 is rotatably coupled to the second cylindrical component 302B. The first arm 306 has a first link 306A that is coupled to the first component 302A, a second link 306B that is coupled to the first link 306A, and a third link 306C that is coupled to the second link 306B. Similarly, the second arm 308 has a first link 308A that is coupled to the second component 302B, a second link 308B that is coupled to the first link 308A, and a third link 308C that is coupled to the second link 308B. The first arm 306 has an operational component 306D coupled to the third link 306C, and the second arm 308 has an operational component 308D coupled to the third link 308C. In addition, the body 302 is also coupled to a support component 310

The first link 306A is coupled to the first component 302A such that the first link 306A can rotate around an axis parallel to the longitudinal axis of the first component 302A. Similarly, the first link 308A is coupled to the second component 302B such that the first link 308A can rotate around an axis parallel to the longitudinal axis of the second component 302B. The second link 306B is coupled to the first link 306A such that the second link 306B can rotate around an axis parallel to the longitudinal axis of the first link 306A. Additionally, the second link 306B can rotate around an axis perpendicular to the longitudinal axis of the first link 306A. Similarly, the second link 308B is couple to the first link 308A such that the second link 308B can rotate around an axis parallel to the longitudinal axis of the first link 308A. Additionally, the second link 308B can rotate around an axis perpendicular to the longitudinal axis of the first link 308A. The third link 306C is coupled to the second link 306B such that the third link 306C can rotate around an axis parallel to the longitudinal axis of the second link 306B. Additionally, the third link 306C can rotate around an axis perpendicular to the longitudinal axis of the second link 306B. Similarly, the third link 308C is coupled to the second link 308B such that the third link 308C can rotate around an axis parallel to the longitudinal axis of the second link 308B. Additionally, the third link 308C can rotate around an axis perpendicular to the longitudinal axis of the second link 308B. The operational component 306D is coupled to the third link 306C such that the operational component 306D can rotate around an axis parallel to the longitudinal axis of the third link 306C. Additionally, the operational component 306D can rotate around an axis perpendicular to the longitudinal axis of the third link 306C.

In this embodiment, the support rods 312A, 312B are held in place within the component 310 (or the component 310 is held in place over the support rods 312A, 312B) using two attachment components 316A, 316B, each of which is configured to attach to one of the support rods 312A, 312B, as shown in FIGS. 5B, 5C, and 5F. In the specific embodiment shown in FIG. 5B, the attachment components 316A, 316B are threaded nuts, and after the support component 310 is disposed over the two support rods 312A, 312B, the threaded nut 316A is threadably coupled to the support rod 312A and the threaded nut 316B is threadably coupled to the support rod 312B to hold the component 310 in place. Alternatively, the attachment components 316A, 316B can be any known attachment components for holding the component 310 in place.

As best shown in FIGS. 5C and 5D, support rod 312A is threadably coupled to support rod attachment 318A. Support rod attachment dove tail 318C is pressed into body pieces 324A, 324B of the first component 302A and by support rod attachment dove tail screws 320A, 320B passing through the support rod attachment dove tail 318C and body pieces 324A, 324B which is then threadably coupled to support rod attachment dove tail nut 322A, 322B. Support rod attachment dove tail nut 322A, 322B is geometrically supported by body pieces 324A, 324B, best shown in FIG. 5 E. The coupled system support rod 312A and support rod attachment 318A are coupled to support rod attachment dove tail 318C such that the coupled system, support rod 312A and support rod attachment 318A, can rotate around an axis parallel to the longitudinal axis of the support rod attachment screw 318B.

As best shown in FIGS. 5F, 5G and 5H, first component motor assembly 326 (encoder 326A, motor 326B, and gearhead 326C) is coupled to first component motor housing 334 by adhesion. The first component motor housing 334 is geometrically coupled to body 324A, 324B of the first component 302A and a clamping force is applied to the first component motor housing 334 from body 324A and body 324B. Body 324A and body 324B are constrained by tongue and groove and elastic bands and tape. First motor gear 328A is coupled to first component motor assembly 326 (specifically gearhead 326C) by interference and D-shaped feature such that it is fixed to the output shaft. First motor bearing set 330A, 303B are seated in the first component motor housing 334. First motor output shaft 332 is rotatably coupled to first motor bearing set 330A, 303B and threadably coupled to first motor output gear 328B. First motor output shaft 332 applies a clamping force to first motor bearing set 330A, 303B to reduce bearing friction.

As best shown in FIGS. 5F and 5G, first component 302A and first link 306A are rotatably coupled. First motor output gear 328B is fixed to first link dove tail 338 by first component mating screws 336A, 336B passing through first motor output gear 328B which are threadably coupled to first link dove tail 338. First link dove tail 338 is geometrically coupled and pressed into first link body 346. First link dove tail screw 340 passes through first link dove tail 338 and is threadably coupled to first link body 346 preventing translation of first link dove tail 338. First link motor cap 344 is geometrically coupled to first link body 346 by tongue and groove and is fixed by first link cap screw 342 passing through first link motor cap 344 which is threadably coupled to first link dove tail 338. First link motor assembly 348 (encoder 348A, motor 348B, gearhead 348C) is adhesively coupled to first link motor tab 354. The coupled system, first link motor assembly 348 and first link motor tab 354c is geometrically coupled to first link body 346. First link direct drive output shaft 352 is geometrically coupled to first link motor assembly 348 by D-shaped feature. First link direct drive output shaft screw 356 is threadably coupled to first link direct drive output shaft 352 and fixes first link motor assembly 348 by applying force to the gearhead output shaft 248D. First link direct drive output shaft 352 is rotatably coupled to first link body 346 by mating the first link direct drive output shaft 352 with the outer race of first link bearing set 350A, 350B and mating the first link body 346 with the inner race of first link bearing set 350A, 350B.

As best shown in FIG. 5H, first link direct drive mating link 360 is fixed to first link direct drive output shaft 352 by geometry and by first link direct drive mating screw 358 passing through first link direct drive mating link 360 that is threadably coupled to first link direct drive output shaft 352. First link direct drive output shaft 352 is geometrically coupled to first link direct drive mating link 360 by D-shaped feature and is fixed by first link direct drive set screw 378 mating with indentation on first link direct drive output shaft 352. First link direct drive set screw 378 is threadably coupled to first link direct drive mating link 360. Second link first motor output shaft 368 is geometrically coupled to second link first motor output gear 364B by interference and D-shaped feature. Second link first motor output gear 364B is rotatably coupled to second link first motor gear 364A. Second link first motor gear 364A is geometrically coupled to second link first motor 362 by interference and D-shaped feature. Second link first motor 362 is geometrically coupled to second link first motor body 374 and is fixed by second link first motor screws 376A, 376B passing through second link first motor gear cap 372A and second link first motor body 374 and is threadably coupled to second link first motor 362, best shown in FIG. 5H-5J. Second link first motor bearing set 366A, 366B is seated in second link first motor body 374 and second link first motor wire cap 372B. Second link first motor output shaft 368 is rotatably coupled with the inner race of second link first motor bearing set 366A, 366B. Second link first motor wire cap 372B is coupled to second link first motor body 374 by tongue and groove. Second link first motor output shaft preload screw 370 is threadably coupled to second link first motor output shaft 368 and passed through second link first motor bearing set 366A, 366B (specifically 366B) and second link first motor wire cap 372B and applies a clamping force to second link first motor bearing set 366A, 366B to reduce bearing friction.

As best shown in FIGS. 5J and 5K, second link second motor 380 is geometrically constrained by second link first motor body 374 and second link second motor housing 384. Second link second motor gear 382A is geometrically constrained by interference and D-shaped feature. Second link second motor gear 382A is rotatably coupled to second link second motor output gear 382B. Second link second motor output gear 382B is geometrically coupled to second link second motor link 390 by interference and D-shaped feature. Second link second motor bearing set 388A, 388B is seated in second link second motor housing 384 and second link second motor gear cap 386. Second link second motor link 390 is rotatably coupled to second link second motor bearing set 388A, 388B. Second link second motor preload screw 394 passes through second link second motor bearing 388B and is threadably coupled to second link second motor link 390 and applies a clamping force to second link second motor bearing set 388A, 388B to reduce bearing friction. Second link second motor gear cap 386 is geometrically constrained to second link second motor housing 384 by tongue and groove and by second link second motor screws 396A, 396B passing through second link second motor gear cap 386 and second link second motor housing 384 which are threadably coupled to second link second motor 380.

As best shown in FIGS. 5L and 5M, second link second motor link 390 is geometrically coupled to third link first motor output shaft 402 by D-shaped feature and is fixed by second link second motor set screw 392 mating with indentation in third link first motor output shaft 402. Second link second motor set screw 392 threadably coupled to second link second motor link 390. Third link first motor 398 is geometrically coupled to third link body halves 412A, 412B and is fixed by third link first motor screws 410A, 410B passing through third link first motor gear cap 400 and third link body halves 412A, 412B and is threadably coupled to third link first motor 398. Third link first motor gear cap 400 is geometrically constrained to third link body halves 412A, 412B by tongue and groove. Third link body halves 412A, 412B are geometrically constrained together by tongue and groove (TG) and elastic bands (EB) and tape, though any appropriate means can be used. Third link first motor gear 408A is geometrically constrained and fixed to the third link first motor 398 by interference and D-shaped feature. Third link first motor gear 408A is rotatably coupled to third link first motor output gear 408B. Third link first motor output gear 408B is geometrically constrained and fixed to third link first motor output shaft 402 by interference and D-shaped feature. Third link first motor bearing set 406A, 406B is seated in third link body half 412A. Third link first motor output shaft 402 is rotatably coupled to third link first motor bearing set 406A, 406B. Third link first motor preload screw 404 passes through third link motor bearing set 406A and is threadably coupled to third link first motor output shaft 402 and applies a clamping force to third link first motor bearing set 406A, 406B to reduce bearing friction.

As best shown in FIG. 5M, third link second motor assembly 414 (314A encoder, 414B motor, 414C gearhead) is coupled to third link second motor housing 422 by adhesion. Third link second motor housing 422 is geometrically coupled to the third link body halves 412A, 412B. Third link second motor gear 420A is geometrically coupled to the third link second motor assembly 414 by interference and D-shaped feature. Third link second motor gear 420A is rotatably coupled to third link second motor output gear/ grasper yoke 420B. Third link third motor 416 is geometrically coupled to the third link body halves 412A, 412B. Third link third motor gear 418A is geometrically coupled to third link third motor 416 by interference and D-shaped feature. Third link third motor gear 418A is rotatably coupled to third link third motor output gear/grasper drive mechanism 418B. Third link second motor bearing set 426A, 426B is seated in third link second motor housing 422. Third link second motor output gear/grasper yoke 420B is rotatably coupled to third link second motor bearing set 426A, 426B. Third link second motor preload nut 430 is threadably coupled to third link second motor output gear/ grasper yoke 420B and applies a clamping force to third link second motor bearing set 426A, 426B to reduce bearing friction. Third link third motor bearing set 428A, 428B is seated in third link third motor housing 424. As best shown in FIG. 5N, third link third motor housing 424 is geometrically coupled to third link third motor 416 and fixed by third link third motor screws 436A, 436B passing through third link third motor housing 424 and are threadably coupled to third link third motor 416. Third link third motor output gear/grasper drive mechanism 418B is rotatably coupled to third link third motor bearing set 428A, 428B. Third link third motor preload nut 432 and third link third motor preload screw 434 is threadably coupled to third link third motor output gear/grasper drive mechanism 418B and applies a clamping force to third link third motor bearing set 428A, 428B to reduce bearing friction.

As been shown in FIGS. 5N-5Q, third link grasper drive shaft 444 is threadably coupled to third link third motor output gear/grasper drive mechanism 418B. Third link grasper drive shaft 444 is geometrically coupled to third link graspers 438A, 438B preventing rotation. Third link grasper drive pin 442 is pressed into third link grasper drive shaft 444 and mates with the gripper slots of the third link graspers 438A, 438B. Third link grasper rotation pin 440 is geometrically coupled on the top side of the third link second motor output gear/grasper yoke 420B passes through the third link graspers 438A, 438B and is threadably coupled to the bottom side of the third link second motor output gear/grasper yoke 420B. When third link third motor output gear/grasper drive mechanism 418B is rotated third link grasper drive shaft 444 translates due to mate with third link graspers 438A, 438B, causing the third link grasper drive pin 442 to move forward in the slots of the third link graspers 438A, 438B, opening the graspers 438A, 438B.

In use, for insertion of device 300 into the body, each arm is positioned, as best shown in FIG. 5R before the robot is inserted. As each robot arm is inserted individually, the forearm 308C is inserted through the single incision first. The upper arm 308B is then inserted to the respective side of the abdominal wall through the incision. The first half of the torso 308A is inserted to the respective side of the abdominal wall through the incision while the first link second motor assembly 348 is actuated negative 45 degrees from the starting position before the next half of the torso 302B is lowered through the incision, as best shown in FIG. 5 S. This process is repeated with the second arm. The support rods 312A, 312B for each of the robotic arms are inserted through the holes in the support rod component 310 until the support rod component 310 mates with each of the torso segments 302A, 302B. A thumb nut 316A, 316B is then threaded onto each support rod 312A, 312B until they become tight against the top of the support rod component 310, locking both arm segments to the support rod component 310.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

The invention claimed is:

1. A robotic device sized to be positioned completely within a patient, the device comprising:
 a. a body component;
 b. a first rotating shoulder component;
 c. a second rotating shoulder component;
 d. a first movable segmented robotic arm operationally connected to the body component by way of the first shoulder component, the first movable segmented robotic arm comprising:
  i. an upper first arm link;
  ii. a lower first arm link;
  iii. a first operational component; and
  iv. at least one first arm motor;
 e. a second movable segmented robotic arm operationally connected to the body component by way of the second shoulder component, the second movable segmented robotic arm comprising:
  i. an upper second arm link;
  ii. a lower second arm link;
  iii. a second operational component; and
  iv. at least one second arm motor; and
 f. an elongate support beam operably coupled to the body component at a distal end of the support beam, wherein the elongate support beam is configured to be positionable through a port into a body cavity of the patient such that a distal portion of the elongate support beam is positioned within the body cavity and a proximal portion of the elongate support beam is positioned outside the body cavity.

2. The surgical robotic device of claim 1, wherein the robotic device may be assembled within the body cavity of the patient.

3. The surgical robotic device of claim 1, further comprising
 a first support rod disposed through a first lumen in the support beam and operably coupled at a distal end of the first support rod with the body component.

4. The surgical robotic device of claim 3, further comprising a second support rod disposed through a second lumen in the support beam and operably coupled at a distal end of the second support rod with the body component.

5. The surgical robotic device of claim 4, wherein the elongate support beam further comprises a third lumen configured to receive at least one connection component.

6. The surgical robotic device of claim 1, wherein the first operational component is chosen from a group consisting of a grasping component, a cauterizing component, a suturing component, an imaging component, an operational arm component, a sensor component, and a lighting component.

7. The surgical robotic device of claim 1, wherein the second operational component is chosen from a group consisting of a grasping component, a cauterizing component, a suturing component, an imaging component, an operational arm component, a sensor component, and a lighting component.

8. The surgical robotic device of claim 1 wherein the at least one first arm motor is configured for operation, rotation or movement of at least one of the first shoulder, the first segmented arm, and the first operational component.

9. The modular surgical robotic device of claim 1, wherein the at least one second arm motor is configured for operation, rotation or movement of at least one of the second shoulder, the second segmented arm, and the second operational component.

10. The surgical robotic device of claim 1, wherein the first and second operational components rotate relative to the first and second segmented arms.

11. The surgical robotic device of claim 1, wherein the first and second segmented arms are capable of jointed movement.

12. A method of performing minimally invasive surgery on a patient, comprising:
 a. providing a surgical robot system comprising:
  i. a robotic device sized to be positionable within a cavity of a patient, the device comprising:
   A. a body;
   B. a first robotic arm having one or more segments;

C. a first shoulder joint disposed between the body and the first robotic arm;
D. a first operational component operably coupled with the first arm;
E. a second robotic arm having one or more segments;
F. a second shoulder joint disposed between the body and the second robotic arm;
G. a second operational component operably coupled with the second arm; and
H. at least one motor housed within the surgical robot;
ii. an elongate support beam comprising at least two lumens;
iii. at least one support rod disposed through one of the at least two lumens, wherein the at least one support rod is coupleable at a distal end of the at least one support rod to the body; and
iv. at least one connection component disposed through another of the at least two lumens;
b. inserting the robotic device into the cavity of the patient in an at least partially unassembled state through a port positioned within an incision in fluid communication with the cavity of the patient;
c. assembling the robotic device inside the cavity of the patient;
d. positioning the elongate support beam through the port such that a distal portion of the elongate support beam is disposed within the cavity and a proximal portion of the elongate support beam is disposed outside of the cavity;
e. coupling a distal end of the elongate support beam and a distal end of the at least one support rod to the body of the device; and
f. performing a procedure with the robotic device supported by the elongate support beam and disposed entirely within the cavity of the patient.

13. A surgical robotic system, comprising:
a. a robotic device sized to be positioned completely within a cavity of a patient, the device comprising:
  i. a device body comprising a first body component and a second body component;
  ii. a first rotating shoulder component operably coupled to the first body component;
  iii. a first movable segmented robotic arm operationally connected to the first shoulder component;
  iv. a first operational component operationally connected to the first robotic arm;
  v. a second rotating shoulder component operably coupled to the second body component;
  vi. a second movable segmented robotic arm operationally connected to the second shoulder component;
  vii. a second operational component operationally connected to the second robotic arm;
  viii. at least one actuator housed within the robotic device; and
  ix. a camera;
b. a support beam comprising at least two lumens, wherein the support beam is coupled at a distal end to the device body;
c. a first support rod disposed within one of the at least two lumens of the support beam; and
d. a first connection component disposed within another of the at least two lumens of the support beam, the first connection component being operably coupled at a distal end to the device body,
wherein the support beam is configured to be positionable through a port positioned within an incision in fluid communication with the cavity of the patient such that a distal portion of the support beam is disposed within the cavity and a proximal portion of the support beam is disposed outside the cavity.

14. The surgical robotic system of claim 13, wherein the actuators are capable of operation, rotation or movement of at least one of the first shoulder, the second shoulder, the first segmented arm, the second segmented arm, the first operational component, and the second operational component.

15. The surgical robotic system of claim 13, wherein the at least one actuator is housed within the group consisting of the first base unit, the second base unit, the first shoulder, the second shoulder, the first segmented arm, the second segmented arm, the first operational component, the second operational component, and the support beam.

16. The surgical robotic system of claim 13, wherein the first and second operational components are chosen from a group consisting of a grasping component, a cauterizing component, a suturing component, an imaging component, an operational arm component, a sensor component, and a lighting component.

17. The surgical robotic system of claim 13, wherein the first and second segmented arms are capable of jointed movement.

18. The surgical robotic system of claim 13, wherein the modular robotic device is assembleable within the body cavity of the patient.

19. The surgical robotic system of claim 18, further comprising an external controller configured to be positioned outside the cavity of the patient, the external controller being operably coupled to the robotic device via the first connection component.

20. The surgical robotic system of claim 13, wherein the support beam further comprises first and second distal legs.

21. The robotic surgical system of claim 20, wherein the first distal leg is operably coupled to the first body component and the second distal leg is operably coupled to the second body component.

* * * * *